US006496713B2

(12) United States Patent
Avrin et al.

(10) Patent No.: US 6,496,713 B2
(45) Date of Patent: Dec. 17, 2002

(54) FERROMAGNETIC FOREIGN BODY DETECTION WITH BACKGROUND CANCELING

(75) Inventors: William F. Avrin, San Diego, CA (US); Peter V. Czipott, San Diego, CA (US); R. Kemp Massengill, Leucadia, CA (US)

(73) Assignees: MedNovus, Inc., Escondido, CA (US); Quantum Magnetics, Inc., San Diego, CA (US)

(*) Notice: Subject to any disclaimer, the term of this patent is extended or adjusted under 35 U.S.C. 154(b) by 0 days.

(21) Appl. No.: 09/960,878

(22) Filed: Sep. 21, 2001

(65) Prior Publication Data

US 2002/0077537 A1 Jun. 20, 2002

Related U.S. Application Data

(63) Continuation-in-part of application No. 09/818,700, filed on Mar. 27, 2001, which is a continuation-in-part of application No. 09/741,774, filed on Dec. 15, 2000, which is a continuation of application No. 09/135,890, filed on Aug. 18, 1998, now Pat. No. 6,208,884, which is a continuation-in-part of application No. 08/670,393, filed on Jun. 25, 1996, now Pat. No. 5,842,986.

(51) Int. Cl.[7] .................................................. A61B 5/05
(52) U.S. Cl. ................... 600/409; 324/207.21; 324/260
(58) Field of Search .............................. 600/407, 409, 600/410; 324/260, 261, 207.11–207.19, 67

(56) References Cited

U.S. PATENT DOCUMENTS

| 4,042,876 A | 8/1977 | Visioli |
| 4,431,005 A | 2/1984 | McCormick |
| 4,709,213 A | 11/1987 | Padhrasky |

(List continued on next page.)

FOREIGN PATENT DOCUMENTS

| DE | 4436078 | 4/1996 |
| EP | 0481211 | 4/1992 |
| EP | 0695531 | 7/1996 |
| GB | 2204133 | 11/1988 |
| GB | 2262606 | 6/1993 |
| WO | WO96/05768 | 2/1996 |

OTHER PUBLICATIONS

Avrin, W.; *Improved Nondestructive Evaluation of Deep, Inaccessible Flaws in Metal Structures*; National Science Foundation Phase I final Report; pp. 1–29; Dec., 1995.

(List continued on next page.)

*Primary Examiner*—Marvin M. Lateef
*Assistant Examiner*—Eleni Mantis Mercader
(74) *Attorney, Agent, or Firm*—Gerald W. Spinks

(57) ABSTRACT

Methods are disclosed for non-invasive screening of the human body by rejecting the magnetic response from biological tissues in the region of interest and outputting data corresponding to the magnetic response of a ferromagnetic foreign body within the region of interest.

34 Claims, 7 Drawing Sheets

U.S. PATENT DOCUMENTS

| | | | |
|---|---|---|---|
| 4,801,882 A | 1/1989 | Daalmans | |
| 4,827,217 A | 5/1989 | Paulson | |
| 4,837,489 A | 6/1989 | McFee | |
| 4,969,469 A | 11/1990 | Mills | |
| 5,057,095 A | 10/1991 | Fabian | |
| 5,099,845 A | 3/1992 | Besz et al. | |
| 5,105,829 A | 4/1992 | Fabian et al. | |
| 5,107,862 A | 4/1992 | Fabian et al. | |
| 5,188,126 A | 2/1993 | Fabian et al. | |
| 5,190,059 A | 3/1993 | Fabian et al. | |
| 5,233,992 A | 8/1993 | Holt et al. | |
| 5,268,165 A | 12/1993 | Hedlund et al. | |
| 5,305,751 A | 4/1994 | Chopp et al. | |
| 5,322,682 A | 6/1994 | Bartzokis et al. | |
| 5,353,807 A | 10/1994 | DeMarco | |
| 5,384,109 A | 1/1995 | Klaveness et al. | |
| 5,408,178 A | 4/1995 | Wikswo et al. | |
| 5,425,382 A | 6/1995 | Golden et al. | |
| 5,456,718 A | 10/1995 | Szymaitis | |
| 5,469,056 A | 11/1995 | Eschner et al. | |
| 5,494,033 A | 2/1996 | Buchanan et al. | |
| 5,494,035 A | 2/1996 | Leuthold et al. | |
| 5,509,412 A | 4/1996 | Bahn | |
| 5,558,091 A | 9/1996 | Acker et al. | |
| 5,610,518 A | 3/1997 | Chamberlain, IV | |
| 5,686,836 A | 11/1997 | Sasada et al. | |
| 5,689,184 A | 11/1997 | Jeffers et al. | |
| 5,705,924 A | 1/1998 | Jeffers | |
| 5,709,225 A | 1/1998 | Budgifvars et al. | |
| 5,735,279 A | 4/1998 | Klaveness et al. | |
| 5,757,183 A | 5/1998 | Smith et al. | |
| 5,957,847 A | 9/1999 | Minakuchi et al. | |
| 6,411,849 B1 * | 6/2002 | Shankar et al. | 607/19 |

OTHER PUBLICATIONS

Avrin, W.; *Magnetoresistive Eddy–Current Sensor for Detecting Deeply Buried Flaws*; Progress in Quantitative Nondestructive Evaluation, vol. 15; Proceedings of Conference in Seattle; pp. 1–6; Jul. 30–Aug. 4, 1995.

Bastuscheck, C.M.; *Technique for Measuring the AC Susceptibility of Portions of the Human Body or Other Large Objects*; J. Appl. Phys. 58(10), pp. 3896–3906, Nov., 1985.

Brittenham, Gary M.; et al.; *Hepatic Iron Stores and Plasma Ferritin Concentration in Patients With Sickle Cell Anemia and Thalassemia Major*; American Journal of Hematology; Jul. 23, 1992; pp. 81–85; vol. 42; Wiley–Liss, Inc.

Brittenham, Gary M., et al.; *Magnetic–Susceptibility Measurement of Human Iron Stores*; The New England Journal of Medicine; Dec. 30, 1982; pp. 1671–1675; vol. 307 No. 27;.

Bryden, F.M.; *Real Time Ultrasound in the Assessment of Intraocular Foreign Bodies*; Eye 4, pp. 727–731; (1990).

Costa Monteiro, E.; *Magnetic Measurement Techniques for Locating Foreign Bodies in Humans*; Tenth International Conference on Biomagnetism, p. 314 (1996).

Farrell, E.J ., *Magnetic Measurement of Human Iron Stores*, IEEE ransactions on Magnetics, vol. MAG–16, No. 5, pp. 818–823, (1980).

Finn, et al., *Ferromagnetic Materials in Patients: Detection Before MR Imaging*; Radiology 156, pp. 139–141 (1985).

Fischer, R. et al.; *Liver Iron Quantification in the Diagnosis and Therapy Control of Iron Overload Patients*; Biomagnetism Clinical Aspects; 1992; pp. 585–588; Elsevier Science Publishers.

Greenblatt, R.E.; *Probabilistic Reconstruction of Multiple Sources in the Bioelectromagnetic Inverse Problem*; Inverse Problems 9, pp. 271–284 (1992).

Kanal, E.; *Aneurysm Clip Testing for Ferromagnetic Properties: Clip Variability Issues*; Radiology, pp. 576–578; (1995).

Mentor Corporation; *The Detector, Injection Port Detection System*; Brochure, 6 pp. (1996).

Paulson, D.N.; *Biomagnetic Susceptometer with SQUID Instrumentation*; IEEE Transaction on Magnetics, vol. 27; No. 2; pp. 3249–3252.

Paulson, D.N.; *The Hamburg Biosusceptometer for Liver Iron Quantification*; Advances in Biomagnetism; pp. 497–500; (date unknown).

Scholz, B., et al.; *Probability–Based Current Dipole Localization from Biomagnetic Fields*; IEEE Transactions on Biomedical Engineering; vol. 41, No. 8; pp. 735–742; Aug., 1993.

Sekihara, K., et al.; *Reduction of Brain Noise Influence in Evoked Neuromagnetic Source Localization Using Noise Spatial Correlation*; Phys. Med. Biol. 39; pp. 937–946;).

Sepulveda, N., et al.; *Magnetic Susceptibility Tomography for Three–Dimensional Imaging of Diamagnetic and Paramagnetic Objects*; IEEE Transactions on Magnetics, vol. 30; No. 6; pp. 5062–5069; (1993).

Shellock, F.G.; *Magnetic Resonance*; Bioeffects, Safety and Patient Management; pp. 115–126; (1996).

Smith, N.; *A High–Sensitivity Magnetoresistive Magnetometer*; J. Appl. Phys. 69 (8); pp. 5052–5084; (1991).

Scholz, B., *Probability–Based Current Sipole Localization from Biomagnetic Fields*, IEEE Transactions on Biomedical Engineering, vol. 41, No. 8, pp. 735–742, (1993).

Wynn, W.M.; *Advanced Superconducting Gradiometer/ Magnetometer Arrays and a Novel Signal Processing Technique*; IEEE Transactions on Magnetics; vol. MAG–11; No. 2; pp. 701–707; (1974).

Thomas, I.M., et al.; *Spatial Resolution and Sensitivity of Magnetic Susceptibility Imaging*; IEEE Transactions on Applied Superconductivity, vol. 3, No. 1, (1992).

* cited by examiner

MR sensor in low-field region between current sheets.

MR Sensor (24)

FERROMAGNETIC FOREIGN BODY DETECTION WITH BACKGROUND CANCELING

CROSS REFERENCE TO RELATED APPLICATIONS

This is a continuation-in-part patent application of U.S. patent application Ser. No. 09/741,774, filed on Dec. 15, 2000, and entitled "Ferromagnetic Foreign Body Detection Using Magnetics", which is a continuation patent application of co-pending U.S. patent application Ser. No. 09/135,890, filed on Aug. 18, 1998; and entitled "Noninvasive Room Temperature Instrument to Measure Magnetic Susceptibility Variations in Body Tissue", now U.S. Pat. No. 6,208,884, which is a continuation-in-part application of U.S. patent application Ser. No. 08/670,393, filed on Jun. 25, 1996, and entitled "Ferromagnetic Foreign Body Screening Method and Apparatus", now U.S. Pat. No. 5,842,986, the disclosure of which is incorporated herein by reference. This is also a continuation-in-part application of co-pending U.S. patent application Ser. No. 09/818,700, filed on Mar. 27, 2001, and entitled "Simplified Water-Bag Technique for Magnetic Susceptibility Measurements on the Human Body and Other Specimens".

STATEMENT REGARDING FEDERALLY SPONSORED RESEARCH OR DEVELOPMENT

The U.S. Government has a paid-up license in this invention as provided for by the terms of Grant Nos. 1 R43 EY11570-01 and 2 R44 EY11570-02A1, and Contract Nos. N43DK-7-2250 and N44-DK-9-2309, all awarded by the National Institutes of Health.

BACKGROUND OF THE INVENTION

1. Field of the Invention

This invention relates generally to an instrument using room-temperature sensors that measure magnetic susceptibility variations in the body of a patient. In particular, the instrument can noninvasively monitor ferromagnetic foreign bodies that may become lodged in a patient.

2. Background Art

There is a need for an accurate, noninvasive method to detect the presence of ferromagnetic foreign bodies in a patient who is being considered for magnetic resonance imaging.

As a matter of interest, biomagnetic susceptometry is a diagnostic procedure that involves noninvasive, radiation-free, direct, and accurate, measurement of the magnetic susceptibility of organs and tissue within a human or animal body. For instance, biomagnetic susceptometry can be used to measure human iron stores contained in the liver, see Harris, J. W., et al. (1978), Assessment of human iron stores by magnetic susceptibility measurements, *Clin. Res.* 26, 540A.; Brittenham, G. M., et al. (1993), Hepatic iron stores and plasma ferritin concentration in patients with sickle cell anemia and thalassemia major, *Amer. J. Hematology* 42, 85; Brittenham, G. M., et al. (1982), Magnetic susceptibility of human iron stores, *New England J. Med.*, 307, 167 1.; Fischer, R., et al. (1992), Liver iron quantification in the diagnosis and therapy control of iron overload patients, *Biomagnetism: Clinical. Aspects*, M. Hoke, et al., eds., Elsevier, Amsterdam, p. 585., 1992; Fischer, R., et al. (1989), in *Advances In Biomagnetism*, S. J. Williamson, et al., eds., Plenum, New York, p. 501. Paulson. D. N., et al. (1991), Biomagnetic susceptometer with SQUID instrumentation, *IEEE Trans. Magnetics* 27, 3249.; and Nielsen, P., et al. (1995), Liver iron stores in patients with secondary hemosideroses under iron chelation therapy with deferoxamine or deferiprone, *Br. J. Hematol.* 91, 827.

Unfortunately, instruments based on Superconducting Quantum Interference Devices (SQUIDs), are complex and expensive. They also use liquid helium, leading to significant operating costs and supply problems. Only a few such devices are in use worldwide presently due to their complexity and expense.

SQUIDs based on the recently developed High-Temperature Superconductors (HTS) could, in principle, reduce the cost of magnetic suceptometry. HTS SQUIDs, which can operate at liquid-nitrogen temperatures, would reduce operating costs, and some of the equipment costs, compared to SQUID devices operating at liquid helium temperatures. However, even at liquid-nitrogen temperatures, the operating costs would be higher than those of ordinary instruments operating at room temperature. Moreover, HTS-SQUIDs are expensive to construct and use, because of the difficulty and low yield of the fabrication process. The difficulties, and the costs, are compounded because these devices are vulnerable to moisture, thermal cycling, and static electrical discharge. HTS-SQUIDs also require the same expensive electronics as conventional SQUIDs.

The present instrument obviates the need for cryogenically cooled SQUIDs by providing operational use at room temperature, making for much less expensive fabrication and use. The instrument allows, generally, for measurements of variations of magnetic susceptibility in a patient and, in particular, for an accurate and inexpensive way of detecting areas of increased magnetic susceptibility in patients. In addition, certain improvements introduced in this invention are applicable to all types of magnetic susceptibility measurements.

A key problem with the magnetic susceptibility method is that the patient's body tissues have their own magnetic susceptibility response, which is superimposed upon the response due to the FFB. To detect the smallest possible FFBs, it would be advantageous to distinguish the signature of the FFB, in the presence of this background response due to body tissues.

U.S. Pat. No. 5,408,178 to Wikswo et. al. describes an apparatus and method for imaging the structure of diamagnetic and paramagnetic objects. The Wikswo et al. method involves applying a magnetic field to a specimen, and measuring the resulting magnetic susceptibility response. Specifically, the Wikswo method attempts to image, or map, the magnetic susceptibility variations within a specimen composed of paramagnetic or diamagnetic material. Wikswo inverts a set of equations, using the measured response as a function of sensor position as well as applied-field direction and measured-field direction, to map out the magnetic susceptibility distribution of the paramagnetic or diamagnetic material within the specimen itself.

The method of the present invention and that of Wikswo et al. make different kinds of measurements and process the data in different ways, to achieve very different results. Specifically, the Wikswo et al. method attempts to image, or map, the magnetic susceptibility variations within a specimen composed of paramagnetic, or diamagnetic material. The present method cancels out the response of paramagnetic or diamagnetic material, to more readily detect the presence of a ferromagnetic foreign body within the specimen. The present method exploits the symmetry properties of the response, as a function of the applied-field and measured-field directions, in order to cancel the response of paramagnetic and diamagnetic material within the specimen, and thus detect the presence of a ferromagnetic foreign body. Wikswo et al. invert a set of equations, using the measured response as a function of sensor position as well as applied-field direction and measured-field direction, in an attempt to map out the magnetic susceptibility distribution of the paramagnetic or diamagnetic material within the specimen itself.

BRIEF SUMMARY OF THE INVENTION

This invention provides a practical method and apparatus for measuring variations of magnetic susceptibilities in a patient, and, in particular, preferably localized areas of increased magnetic susceptibility. The probing instrument's distal end assembly includes a room temperature functioning magnetic sensor that can detect the characteristic magnetic response from tissue to a magnetic field supplied by an applied-field coil, or a permanent magnet, that is also part of the instrument's distal end assembly. The applied field coil can be an alternating current (AC) coil. The magnetic susceptibility measurements have sufficient resolution to monitor small variations in magnetic susceptibility within the patient, when the instrument is placed external to the patient.

The applied field may be produced using an applied field coil or a permanent magnet. The use of an applied field coil is preferred for a number of reasons. First, it lends itself to the application of an alternating magnetic field. The use of an alternating magnetic field reduces sensor noise, reduces noise due to ambient magnetic fields, and facilitates the modulation of the sensor-sample distance in order to reduce the effects of temperature drift in the sensing apparatus. Also, the use of an applied-field coil, or coils, lends itself to the cancellation of the signal due to the applied magnetic field.

An alternative embodiment is to use a permanent magnet to produce the applied magnetic field. A permanent magnet produces a constant DC field, which lacks many of the advantages of an alternating field. In principle, one could produce an alternating magnetic field by appropriate movement, such as reciprocating motion, of one or more permanent magnets.

The magnetic sensor can be, but is not necessarily limited to, a magnetoresistive sensor, including giant magnetoresistive and spin-dependent tunneling sensors, a fluxgate magnetometer, or a magneto-inductive sensor. In some cases, the noise in the magnetic field measurements can be reduced by using an induction coil sensor, which detects a changing magnetic field by measuring the voltage induced in a coil of electrically conductive wire.

The applied field coil dimensions are such that an applied field is optimized for maximum response from localized areas of interest in the body. In particular, the instrument is preferably designed for detecting the presence of ferromagnetic foreign bodies (FFBs) in a patient. For this application, the applied field coil dimensions are optimized to maximize the magnetic susceptibility response from the item of interest and minimize effects caused by the overlying tissue. To minimize noise introduced in the magnetic measurements due to fluctuations in the applied field, the applied-field coil and/or magnetic sensors are configured so as to cancel the signal due to the applied field. Both the real and imaginary parts of the applied field signal are canceled. This result can be achieved by designing the applied-field coil so that the field is canceled at the position of the sensor. Alternatively, the magnetic sensor itself can be designed as a magnetic gradiometer, so as to cancel the signal due to the applied field.

The probe instrument's distal end detector assembly includes one or more applied field coils and magnetic sensors, in a geometry designed to cancel the applied-field signal and to maximize the signal due to the objects of interest in relation to that of overlying body tissue. The magnetic sensor is preferably a magnetoresistive (MR) sensor or an induction coil. In general, MR sensors are preferred where the frequency of the AC field is low, and where it is necessary to sense the magnetic field within a relatively small volume, while induction coils are preferred where the frequency is high, and it is possible to average the magnetic field over a relatively large volume or surface area. When an MR sensor is used, a feedback coil can be mounted on the sensor, which "locks" the sensor at its optimum operating point by applying a compensating field to cancel changes in the ambient field, thus maintaining a constant sensitivity of the detector assembly. This feedback technique is desirable in some cases to maintain constant responsivity and high linearity, especially in instances where it is necessary to measure small changes in magnetic field in the presence of much larger background magnetic fields.

The probing instrument's magnetic sensor control electronics, an applied field source signal generator, a lock-in amplifier, an audio amplifier, and an FFT spectrum analyzer or equivalent computer device for signal analysis can all be incorporated in a single medical instrument housing for field use. A computer can be used to perform the functions of the signal generator, the lock-in amplifier, and/or the FFT spectrum analyzer. The computer approach may reduce cost, especially in cases where measurements with multiple sensors are required.

A physician uses the probing instrument by positioning the probe's distal end adjacent to an area of interest, such as the eye/orbit, and the probe instrument then analyzes the observed signal, and outputs data corresponding to material of interest.

Further, according to the present invention, the magnetic responses of surrounding body tissues are canceled out, allowing the presence of a ferromagnetic foreign body to be detected easily. This tissue background cancellation can be achieved by two methods. The first method determines whether the measured magnetic field response falls outside a normal range determined from a statistical analysis of measurements on a population of subjects. This analysis exploits statistical regularities in the responses of normal subjects, including, for example, the similarity in response between the left and the right sides of the patient's head.

The second method determines whether the magnetic field response exhibits certain mathematical symmetries that reflect the weak, isotropic magnetization properties characteristic of biological tissues.

The second method applies uniform magnetic fields to the target region, in each of three orthogonal directions. For each direction of the applied field, the magnetic field response of the specimen is measured. Preferably, the magnetic field in each of three orthogonal directions is measured, for each direction of the applied magnetic field. However, useful information can be obtained by measuring the magnetic field solely in the direction of the applied field. Other combinations of applied field and measured field are possible as well. Measuring the magnetic field in all three directions maximizes the probability of detecting a ferromagnetic foreign body, regardless of its orientation, location, and shape. All of these magnetic-field measurements are made at the same sensor location. The results are expressed as a matrix or table of values, where each entry By represents the magnetic field response measured in the direction i, while applying the magnetic field in the direction j. If the specimen contains only paramagnetic or diamagnetic material, that is, material whose magnetization is proportional to, but weak in comparison to, the applied field, this matrix will be symmetric and traceless, that is, Bij−Bji= O, and $B_{11}+B_{22}+B_{33}=0$. Using these symmetry properties, one can cancel out the response of the diamagnetic and paramagnetic material within the specimen, leaving only the response due to a ferromagnetic foreign body contained within the specimen. In the present method, the applied magnetic field is uniform and unidirectional, in order that the matrix By have the required symmetry properties.

Depending on the particular combination of applied and measured fields that is used, it may occur that a ferromagnetic foreign body with a particular combination of shape, orientation, and location may not be revealed by examining the quantities, Bij−Bji, and $B_{11}+B_{22}+B_{33}$. In order to avoid such situations, it is desirable to repeat the entire measurement sequence described above, varying the sensor location with respect to the patient. It should be noted that this variation of the sensor location has a different purpose in the present method than in the method of Wikswo et al. Wikswo et al. measure the magnetic field response at a plurality of sensor locations, in order to derive a map of the spatial variation of magnetic susceptibility within the sampled region. In the present invention, the sensor location is varied in order to change the spatial relationship between the ferromagnetic foreign body and the magnetic sensor, or sensors, so as to ensure that at least one of the quantities, Bij−Bji, or $B_{11}+B_{22}+B_{33}$, is nonzero for at least one sensor location. As indicated previously, the present invention does not rely on mapping magnetic susceptibility variations within the sampled region. Rather, the present approach is to cancel the response of the host tissue without canceling the response of the ferromagnetic foreign body. This affords a simpler solution to the problem of FFB detection than the method of Wikswo et al.

As will be discussed below under the heading, "Data Analysis Combining both Discrimination Techniques," the two methods described above can be combined into a single statistical analysis framework.

In addition to these background discrimination techniques, the variability of the magnetic response of the host can be minimized by inserting between the patient and the sensing instrument a bag, or other compliant container filled with water, a gel, or other material, which will conform to the shape of the sensed region, such as the eye/orbit, and which approximates the magnetic susceptibility of the sensed body region. Water-bag techniques have been used previously in the context of liver iron measurements. However, the present invention encompasses a novel water-bag method which has significant advantages when used with a room temperature sensor system.

Further, with any of these discrimination techniques, telemedicine can be employed to enhance the functionality of the techniques. The preferred vehicle for telemedicine is the Internet. Artificial intelligence modalities, including neural networks and other expert systems, such as rule-based systems, can also be employed, providing instantaneous auto-interpretation of test results. Real time interactive feedback is thus provided between a remote test instrument and a central computer processing system, thereby helping to ensure patient cooperation and reliable data acquisition.

The novel features of this invention, as well as the invention itself, will be best understood from the attached drawings, taken along with the following description, in which similar reference characters refer to similar parts, and in which:

DETAILED DESCRIPTION OF THE INVENTION

Figure 1:
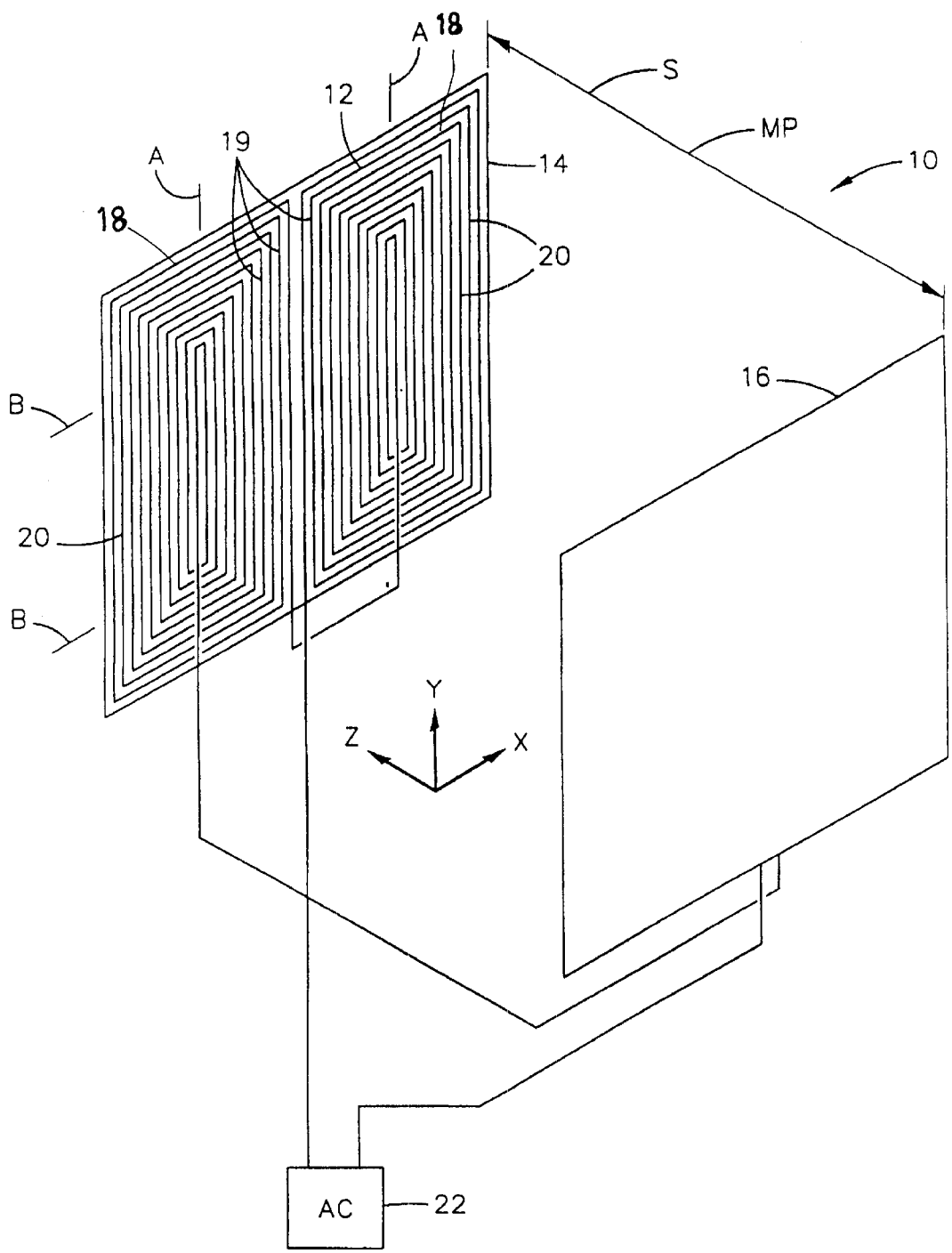
FIGS. 1, 2 and 3 show features of a magnetic susceptibility detector, which includes the applied field coil with a magnetic sensor, as disclosed in parent U.S. Patent application Ser. No. 08/670,393, now U.S. Pat. No. 5,842,986.

Provided herein is a room-temperature medical probing instrument that measures variations of magnetic susceptibility. The invention's probe instrument can make magnetic susceptibility measurements with a very small degree of uncertainty.

Performance of the room-temperature instrument depends on two critical issues:

a) The instrument has to be sensitive enough to see the small magnetic signals produced by the magnetic susceptibility of the item of interest; and b) The magnetic susceptibility of the item of interest has to be determined accurately in the presence of the interfering signal produced by the slight magnetic susceptibility of the overlying tissue and other surrounding tissues.

In magnetic susceptibility measurements, a magnetic field is applied, inducing a magnetization in the area of interest. A small magnetic field produced by this sample magnetization is then detected using a magnetic sensor. The sample magnetization depends upon the intensity of the applied field and upon the magnetic susceptibility of the materials present within the sensed region.

In magnetic susceptometry, very weak susceptibilities are sometimes encountered. For comparison, in liver susceptometry, the difference in magnetic susceptibility between the liver and surrounding tissue is proportional to the liver iron concentration. The main iron compound stored in the liver has a susceptibility of approximately $1.6 \times 10^{-6}$ (in SI units) per milligram of iron per cubic centimeter of liver. Typical patients with iron overload have several milligrams of iron per cubic centimeter of liver. The instrumental noise of existing SQUID biosusceptometers corresponds to an uncertainty of about 20 micrograms per cubic centimeter in liver iron concentration. Factors including uncertainty in the magnetic susceptibility of surrounding tissues contribute sources of systematic uncertainty in clinical liver measurements. Clinical measurements with existing SQUID-based instruments achieve uncertainties in the range of 0.2 to 0.5 milligrams of iron per gram of liver, which corresponds to a magnetic susceptibility resolution of 3 to $7 \times 10^{-7}$ (SI Units).

To detect a weak magnetic response, there are two technical issues:

a) Minimization of noise in the detector's magnetic-field sensors (and, to a lesser extent, the background noise from the environment) so that detection of the magnetic response can be performed without applying excessively large fields; and b) Ensuring that the spurious signals due to the applied fields are small compared with the desired magnetic susceptibility signal.

With respect to sensor noise requirements, in order to measure a given magnetic susceptibility, the applied field must be large enough and the noise from the magnetic sensor must be low enough so that the magnetic susceptibility response is much greater than the sensor noise. In practice, using a room-temperature instrument, the applied field is limited by the need to avoid excessive ohmic heating in the applied field coils of the detector assembly. Excessive heat loads can induce thermal drifts in the geometry of the applied field coils. As discussed below, such drifts could affect the ability to suppress spurious signals due to the applied field. However, an applied magnetic field of roughly $10^{-3}$ T to an area of interest does not incur excessive thermal drift effects.

If a field of $10^{-3}$ T is applied, and the magnetic field due to the response of the sample is $10^{-7}$ times the applied field, then the magnetic sensor noise must be less than $10^{-10}$ Tesla. Such noise requirements can readily be met using room-temperature functioning magnetic sensors, such as a magnetoresistive (MR) sensor with very low noise. Such sensors are commercially available from Honeywell, Phillips, and other companies. A variety of other sensor types could also meet the requirements of the present invention, including other sensors based on magnetoresistance, such as giant magnetoresistance sensors and spin dependent tunneling sensors, as well as fluxgate magnetometers, magnetoinductive sensors, and induction coils.

To measure very weak magnetic signals, care is required to ensure that magnetic noise from the environment does not obscure the magnetic signal being measured. However, environmental magnetic noise is generally less of a problem in the AC magnetic measurements used in the present invention than in the DC magnetic measurements used in existing SQUID biosusceptometers, which convert the dc magnetic response into a time-varying magnetic signal by moving the patient up and down. However, this modulation takes place at a rather low frequency, generally less than 1 hertz. At such low frequencies, the background noise in many environments is quite large, such that SQUID systems often face a formidable problem of environmental noise rejection.

The present invention's room-temperature system preferably applies an AC magnetic field at a frequency between around 25 and 2,000 hertz, and detects the magnetic response at the same frequency. At these frequencies, environmental background fluctuations are usually small, as long as noise peaks at harmonics of the power-line frequency are avoided, so that the need for environmental noise rejection is greatly reduced.

Magnetic signal measurements needed for the probe instrument are $10^7$ times smaller than the field applied to a patient's body. In making such a measurement, technical issues include the stability of the applied magnetic field, the stability of the magnetic sensors, and the geometrical stability of the magnetic-field coils and sensor array.

The present instrument is designed so that fluctuations of the current in the applied-field coil have only a negligible effect on the magnetic measurements. The invention uses a detector assembly whose applied field coil is geometrically configured such that almost no magnetic field occurs at a location where the magnetic sensor is positioned in relation to the applied field coils. If the magnetic sensor were exposed to the full amplitude of the applied field, then the current in the field coils would have to be stable to at least one part in $10^7$ to resolve the weak magnetic signals observed in magnetic susceptibility measurements. However, if the detector's sensor observes only $10^{-4}$ of the field applied to the sample, the coil current can vary by as much as one part in $10^4$, and the corresponding variations in the magnetic measurements are then only $10^{-8}$ of the field applied to the sample.

Figure 2:
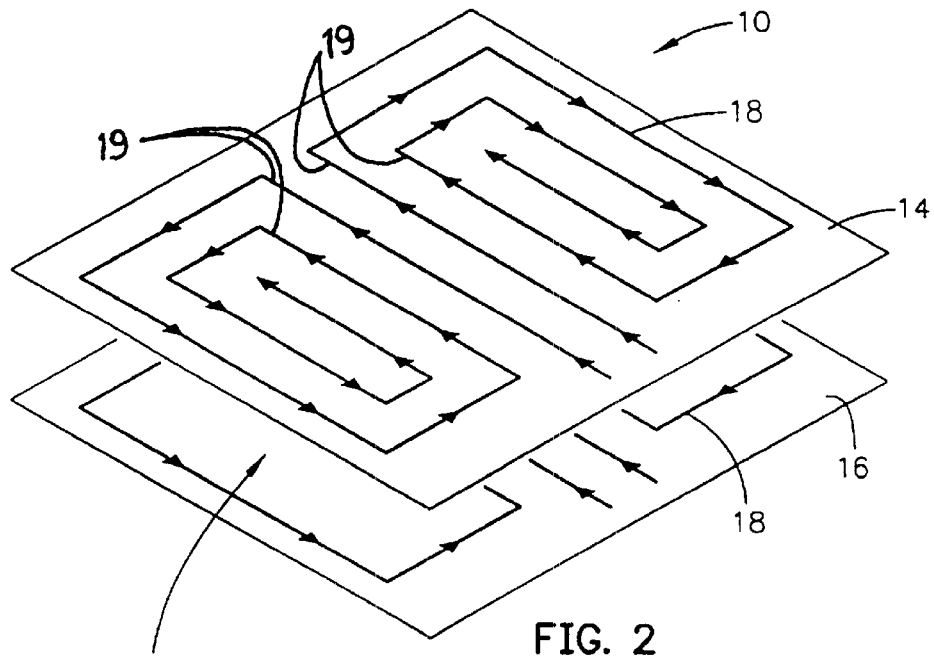
Figure 3:
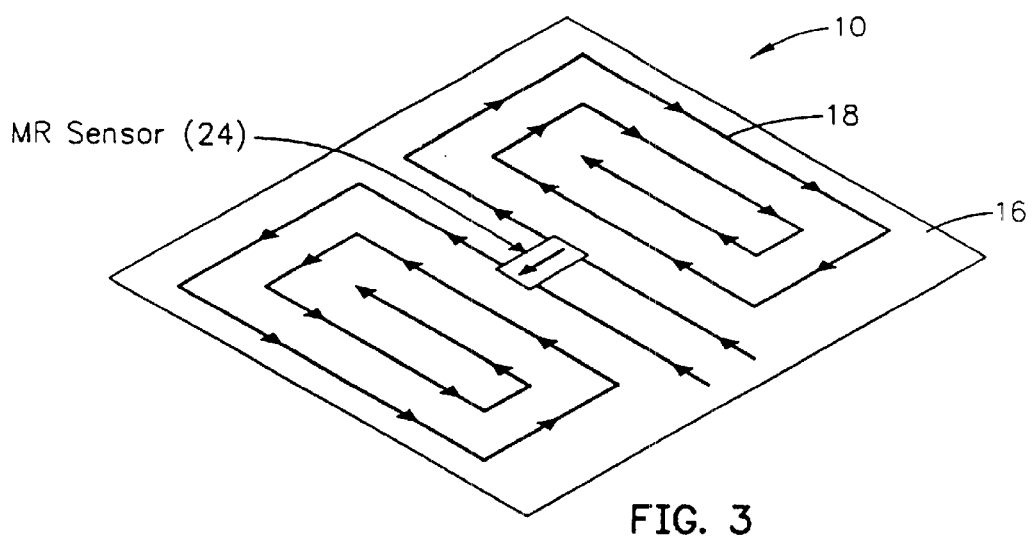

FIGS. 1, 2 and 3 show the applied field coil and magnetic sensor design and system for determining FFB objects as disclosed in parent U.S. patent application Ser. No. 08/670,393 of Avrin et al., entitled "Ferromagnetic Foreign Body Screening Method and Apparatus", now U.S. Pat. No. 5,842,986. The detector assembly 10 makes use of the technical principles discussed above. This detector assembly 10 provides magnetic susceptibility measurement information available for the detection of retained ferromagnetic foreign body (FFB) objects, that is metallic objects inside human tissue, as a way of screening patients prior to magnetic resonance imaging (MRI) or other medical procedures. This detector assembly 10 can also be used in the invention herein.

System components also include equipment for using magnetic measurement signals from the sensors to detect and locate ferromagnetic objects, and for distinguishing the signals of the target objects from other interfering magnetic fields.

Below, the detector assembly in the parent U.S. patent application Ser. No. 08/670,393 is first described, followed by a description of the exemplary instrument design for improved detection characteristics.

FIGS. 1, 2, and 3 collectively show a detector assembly 10 which is intended to be placed near the body region to be screened. The applied field coils 18, when supplied with a current from the current signal generator 22, generate a time-varying applied magnetic field to the body. The magnetic material in the body region responds, providing a small magnetic field that is detected by a sensor 24 (shown in FIG. 3) or array of sensors (not shown) positioned adjacent to the body region. Together, the applied field coils 18 and the sensor(s) 24 allow measurement of anomalies in the magnetic susceptibility of the body region being screened. In particular, the geometry of the applied field coils and the placement of the magnetic sensor(s) is such that the interfering applied field experienced by the magnetic sensor(s) 24 is as small as possible. As discussed earlier, this arrangement reduces the interfering signal produced by the varying magnetic field. The detector assembly consisting of the sensor(s) 24 and applied field coils 18 can be stationary, or can be movable to generate a magnetic susceptibility anomaly map over the body part being screened. The intensity and the time dependence or frequency dependence of the magnetic susceptibility anomaly can be interpreted rapidly by a signal processor to reveal the location and size of ferrous metallic objects retained within the screened body region.

The applied magnetic field may be several orders of magnitude larger than the signal of the FFB object(s). One arrangement of the device 10 is to configure the applied field coils 18 so that the applied field is nearly canceled out in regions within the device 10, within which the magnetic sensors 24 are positioned and attached (FIG. 1). The applied field coil element 12 is laid out on the surfaces of two printed circuit (PC) boards 14, 16. The two PC boards 14, 16 are placed parallel to each other, with the magnetic sensors placed between the two PC boards 14, 16. Each PC board 14, 16 accommodates a multiplicity of parallel, evenly spaced current paths 19 traveling in one direction in the center region of the board, with return paths 20 along the outer edges of the board, approximating two spiral patterns. The spiral patterns on one PC board are connected in series so that, when a current is passed through them, the resulting electric current distribution approximates a uniform sheet of current flowing in the y-direction as shown, over a substantial region near the center of the board. This region of the board is roughly defined by the area between the markers A-A and between the markers B-B. This current distribution produces a magnetic field that is nearly uniform over a region of space near the center of the board. The two boards 14, 16 of this design are placed parallel to each other, with this relationship being shown. The PC boards 14, 16 are separated by a distance S which is small compared with the length and width of the central region of uniform current. The two PC boards 14, 16 are mounted so that the current paths 19 on one board are oriented parallel to the corresponding current paths 19 on the other board. The current paths on the two boards 14, 16 are then connected in series to an AC signal generating power supply 22, so that the current flows in the same direction on both boards, the y-direction in the arrangement shown. The source 22 can be equipped with a control device, as is known in the art, to cause the field to be pulsed, to vary in frequency, or to have a waveform with multiple frequencies. These time variations in the applied field can assist in distinguishing the magnetic response of the sensed region from the environmental background magnetic fields, by synchronization of the sensing circuitry with the power supply. In a region surrounding the centers of the two PC boards 14, 16, the magnetic field produced by this arrangement approximates that produced by a pair of parallel, uniform sheets of current flowing in the y-direction. In the space between the centers of the two PC boards, the net magnetic field is nearly zero since the contributions from the two current sheets approximately cancel each other. There is a small residual magnetic field, since perfect field cancellation is prevented by the finite size of the current sheets, and the presence of the return paths 20 along the outer edges of the PC boards 14, 16. However, due to the symmetry of the current paths in the two PC boards, the magnetic field is substantially zero in the plane midway between two PC boards. The magnetic sensor(s) 24 are placed in a plane parallel to the PC boards 14, 16, with the plane of the sensors being located at the midpoint MP between the two PC boards 14, 16, so that the sensors are nearly in a zero field state with respect to magnetic fields generated by the applied field coils 18.

FIG. 2 shows another view of the sandwiched field coil with a magnetic sensor 24, placed in a low-field region between parallel circuit boards 14 and 16 as shown in FIG. 1. This magnetic sensor could be an MR sensor as shown, or, alternatively, a coil or other suitable magnetic sensing device. The current paths are shown with lines and arrows. The magnetic sensor 24 is sandwiched between two printed circuit boards 14, 16. The central region of each circuit board 14, 16 contains a number of parallel, evenly spaced traces 19 which are connected in series and which carry identical applied field currents.

FIG. 3 shows where the magnetic sensor 24 is placed with respect to the applied field coil 18. The top coil has been removed to show sensor positioning. The arrow on the sensor 24 indicates the direction of its field sensitivity. Various methods may be used to null out the field at the sensor location. For example, a set of shims may be used to adjust the position of the sensor between the two current sheets. This adjustment is useful because the applied field, given the finite size of the circuit boards 14, 16 used, is zero only on the plane of symmetry midway between the two current sheets. With this coarse adjustment, a reduced residual field occurs at the sensor to a value roughly 300 times smaller than the field at the outer surface of the coil set. A fine balance adjustment may then be made by placing small tabs of metal near the sensor. By using balance tabs of both steel and aluminum foil, the in-phase and the out-of-phase components are canceled out of the magnetic field with respect to the ac current supplied to the applied field coil. A reduced residual field to a level roughly 30,000 times smaller than the field at the outer surface of the coil set occurs when current is applied. Any noise due to the variations in the ac supply current is less than $10_{-8}$ of the field applied to an examined sample, that is the tissue.

In the detector 10, geometrical variation of the applied field coils 18 and sensor(s) 24 is an important effect that this field-nulling system cannot remove. Temperature variations may cause subtle distortions in the geometry of the applied-field coils, or in the position of the magnetic sensor within the coils. Such distortions can perturb the balance of the field-canceling system, producing noise in the magnetic measurements.

The detector assembly can minimize effects caused by geometric distortion of the detector assembly, by modulating a distance between an area of interest and the instrument's detector assembly at up to several hertz, with displacement of the detector assembly up to six inches. The change in the magnetic signal at the modulation frequency is then measured. This departs from methods used with conventional SQUID devices by moving the detector assembly 10 while the patient remains stationary. The instrument can perform this function by mounting the detector assembly, which includes the applied field coils 18 and the sensor 24, on a nonmagnetic platform, and oscillating the detector assembly 10 back and forth at several hertz using a motor. The motor can drive a mechanism for producing oscillatory movement of the detector assembly. This mechanism can be a cam driven, spring biased plate, where the cam member is belt driven by the motor, or a reciprocating rod where the detector assembly is mounted to a plate that oscillates by a linear drive member. Other reciprocating motion-type devices can be used as well to provide proper oscillatory motion with displacements of up to and around six inches, at motion frequencies up to and around 10 hertz. The detector assembly is mounted in a housing that provides support and positioning for the instrument. The housing and the components of the oscillatory motion mechanism are made of nonmetallic, nonmagnetic materials. Signal analysis described below extracts information from the detector assembly 10 signal output from the magnetic sensor 24.

The ability to move the detector assembly 10 instead of the patient is significant since the overall instrument is much simpler and less expensive. Moving a SQUID type magnetic sensor is not permitted since any magnetic gradients in the environment produce signals that interfere with the direct current magnetic response measurements. These ambient magnetic gradients do not present problems in the proposed invention's measurements. For example, the room temperature sensor(s) 24 have much more tolerance compared to SQUIDs when being moved in the presence of the earth's magnetic field.

In many applications, including the detection of ferromagnetic foreign bodies, it is desirable to maximize the magnetic response from the item or region of interest with respect to the magnetic response from the overlying tissue.

Figure 4:
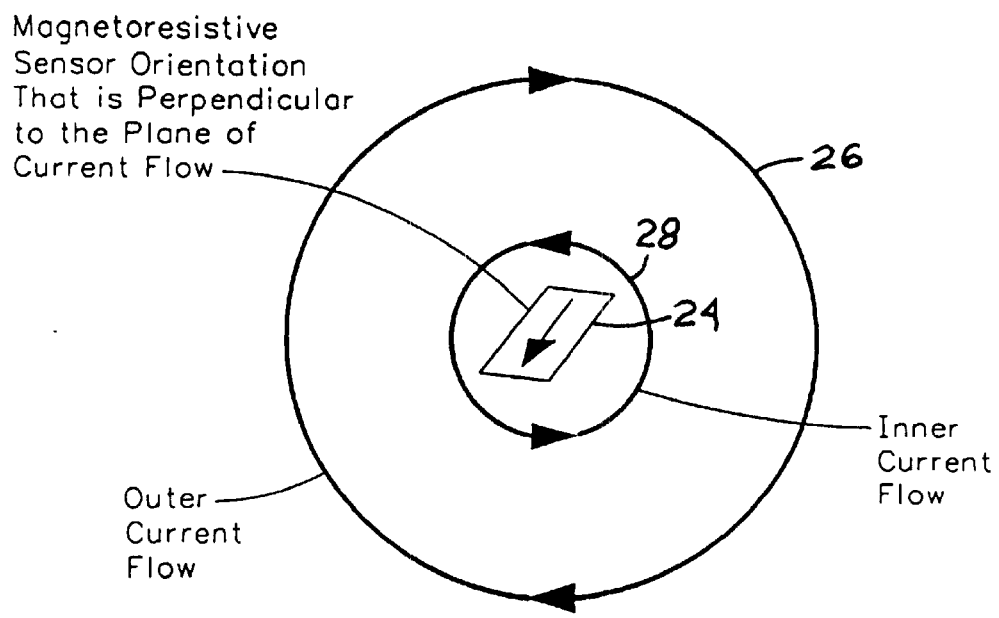
FIGS. 4 and 5 show features of a magnetic susceptibility detector, which include the circular applied field coils and center mounted magnetoresistive sensor used in the probing instrument, as disclosed in U.S. patent application Ser. No. 09/135,890, now U.S. Pat. No. 6,208,884.
Figure 5:
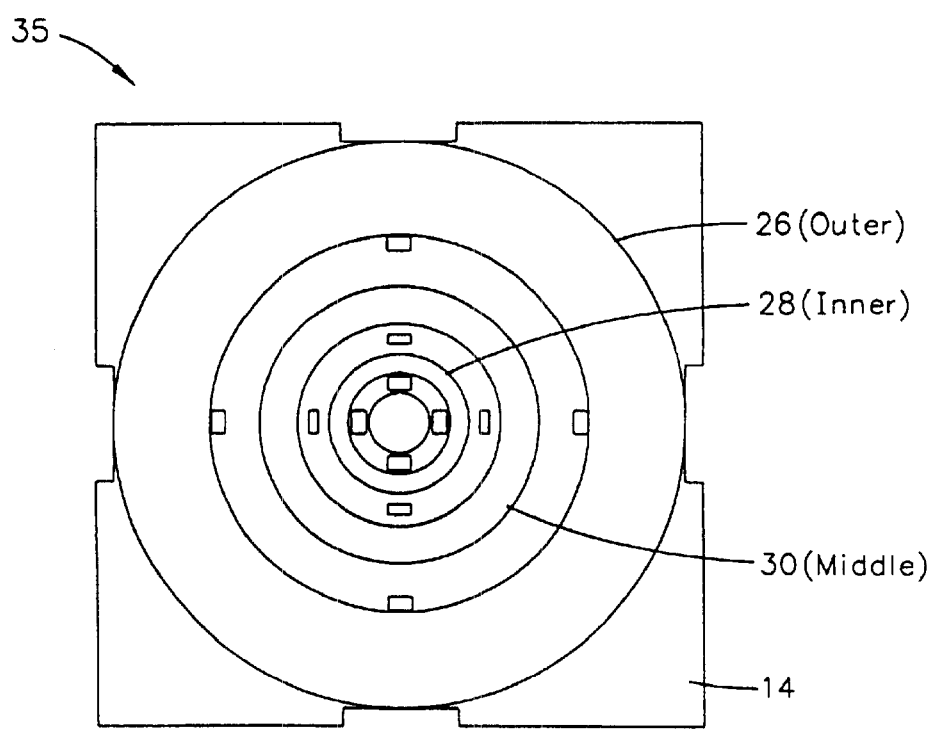

FIGS. 4 and 5 show the design of an applied field coil arrangement 35 whose geometrical design makes it possible to evaluate, and thus to subtract out, the magnetic response of overlying tissues, as described in U.S. patent application Ser. No. 09/135,890, now U.S. Pat. No. 6,208,884. This design is potentially useful in a variety of applications, including for ferromagnetic foreign body detection. Such a design adjusts the diameter of the applied field coils 26,30 to control how deeply the applied magnetic field penetrates into the patient's body. A circular coil of radius "a" produces a field that falls off rather slowly out to distances comparable to "a" and then decays as $1/r^3$ at longer distances. The two main field coils 26,30 allow for measurement of the response of the item of interest, and evaluation of the response due to the susceptibility of the overlying tissues.

FIG. 5 shows the detector assembly's applied field coil arrangement. The applied field coil in the detector assembly comprises three concentric circular spiral coils, but can include additional coils for designs that encompass the present invention's design. FIG. 5 shows the first coil 26, with a relatively large diameter, which produces a field that reaches deep into a patient's body. The resulting magnetic susceptibility response contains contributions from both the item of interest and the overlying tissues.

The diameter of this coil 26 maximizes the contribution of the item of interest and minimizes the overlying tissue contribution, so that variations in the susceptibility of the overlying tissue have as little effect as possible on the measurement of susceptibility of the item of interest. A mean diameter in a range of around 15 to 50 cm for the outer coil 26 is preferred.

FIG. 5 shows the small, innermost applied field coil 28. During magnetic susceptibility measurements, this smaller coil is connected in series with the outer coil 26, in such a way that the current in the inner coil 28 is in the opposite direction from that in the outer coil 26. The diameters and numbers of turns in the two coils are adjusted so that the magnetic field due to the inner coil cancels the magnetic field due to the outer coil, in a region near the common center of the two coils, producing a small zone of substantially zero magnetic field. The magnetic sensor (24 in FIG. 4) is then placed in this zone of substantially zero magnetic field so that, as discussed above, fluctuations of the current in the applied field coils produce very little noise in the magnetic susceptibility measurements. The inner coil can have a mean diameter of about 1.5 to 8 cm. Since the magnetic field due to the small, innermost coil 28 dies away rapidly with distance, the magnetic field in the patient's body tissues is produced almost entirely by the outer coil 26.

FIG. 5 also shows the intermediate-diameter coil 30 which can optionally be used, in place of the outer coil 26, to produce a magnetic field that reaches a relatively short distance into the patient's body. Magnetic susceptibility measurements made using this intermediate-diameter coil 30 will produce a magnetic susceptibility response whose main contribution comes from the patient's overlying tissues. The results of these measurements can be used to evaluate the magnetic susceptibility of the overlying tissues. This information can then be combined with the results of magnetic susceptibility measurements made using the outer coil 26, to evaluate the magnetic susceptibility of the item of interest, while removing errors due to the susceptibility of the overlying tissues. In magnetic susceptibility measurements made using the intermediate-diameter coil 30, the intermediate-diameter coil 30 is connected in series with the small, inner coil 28, in such a way that the magnetic field is canceled at, the location of the magnetic sensor.

FIG. 5 shows exemplary dimensions of the three concentric coils that make up the applied field coil. Each coil consists of one or more concentric loops. The number of loops in each coil is proportional to its diameter. This ensures that if any two coils are energized with equal but opposite current, the field at the center will be zero. This equal and opposite current is realized by making the appropriate electrical interconnections between the inner and outer coils and applying current to the two coils using the same current source. In this example, the outermost coil 26 has exactly four times the diameter of the innermost coil 28, and has exactly four times as many turns. When magnetic susceptibility measurements are made using the outer coil 26, this coil is connected in series with the innermost coil 28, but with opposite polarity, as shown in FIG. 4 by the two oppositely directed arrows. The magnetic field cancels out almost completely at the location of the detector 10. The intermediate-diameter coil 30 has exactly twice the diameter, and twice the number of turns, as the innermost coil 28. When measurements are made using this intermediate coil 30, it is connected in series with the innermost coil to cancel out the magnetic field at the sensor 24 location.

The applied field coils 26,28,30 can comprise traces on a printed circuit board. To generate the maximum field for a given current magnitude, similar coil sets can be positioned on both sides of the circuit board 14, thus doubling the number of turns of each coil. In addition, stacks of circuit boards 14 can provide sufficiently strong field to the examined tissue sample, without the excessive ohmic heating (and the resulting undesirable thermal drifts) that can occur if too large a current is passed through a single circuit board. Alternatively, the printed circuit board can be replaced by wires, metal rods, or other electrical conductors supported by a rigid support structure that maintains the appropriate spatial relationship of the current carrying elements.

FIG. 5 shows a PC board 14 which has a number of circular holes for bolting individual boards together rigidly to a solid G-10 fiberglass plate for structural stability. The larger noncircular holes facilitate electrical connections between the coils 26,28,30 on the stacked circuit boards. A hole at the center of the coil set allows for placement of a sensor 24 in a low field region close to the sample. The magnetic sensor 24 is placed in the appropriate orientation so as to sense magnetic fields normal to the plane of the applied field coils (as indicated by FIG. 4). In this zero-field region, the sensor is practically immune to the applied field directly and only senses the body's response to the applied field.

In an example of the design shown in FIG. 5, the outer coil 26 consists of 16 equally spaced concentric loops with a mean diameter of 20 cm. The inner coil 28 consists of 4 equally spaced concentric loops with a mean diameter of 5 cm. The middle coil 30 has 8 equally spaced concentric loops with a mean diameter of 10 cm. The applied field coil design ensures that when any pair of coils is energized with equal and opposite current the applied field at the center of the coils is zero.

The contribution of the overlying tissue to the signal can be measured and subtracted out by using the middle coil 30. Since the middle coil is smaller than the outer coil, the magnetic field generated by the middle coil will not penetrate as deeply into the body as will the field generated by the outer coil. Therefore, with the proper choice of coil dimensions, the response signal due to the applied field of the middle coil will be mostly due to the overlying tissue closer to the surface of the body, whereas the response signal due to the applied field of the outer coil will be due to both the item of interest and the overlying tissue. Consequently, two successive magnetic susceptibility measurements, using the outer coil and the middle coil, provide two independent pieces of information, which can be used to solve mathematically for two unknown quantities, the magnetic susceptibilities of the item of interest and the overlying tissue. This method determines the magnetic susceptibility of the item of interest, while removing errors due to variability in the magnetic susceptibility of the overlying tissue.

Figure 6:
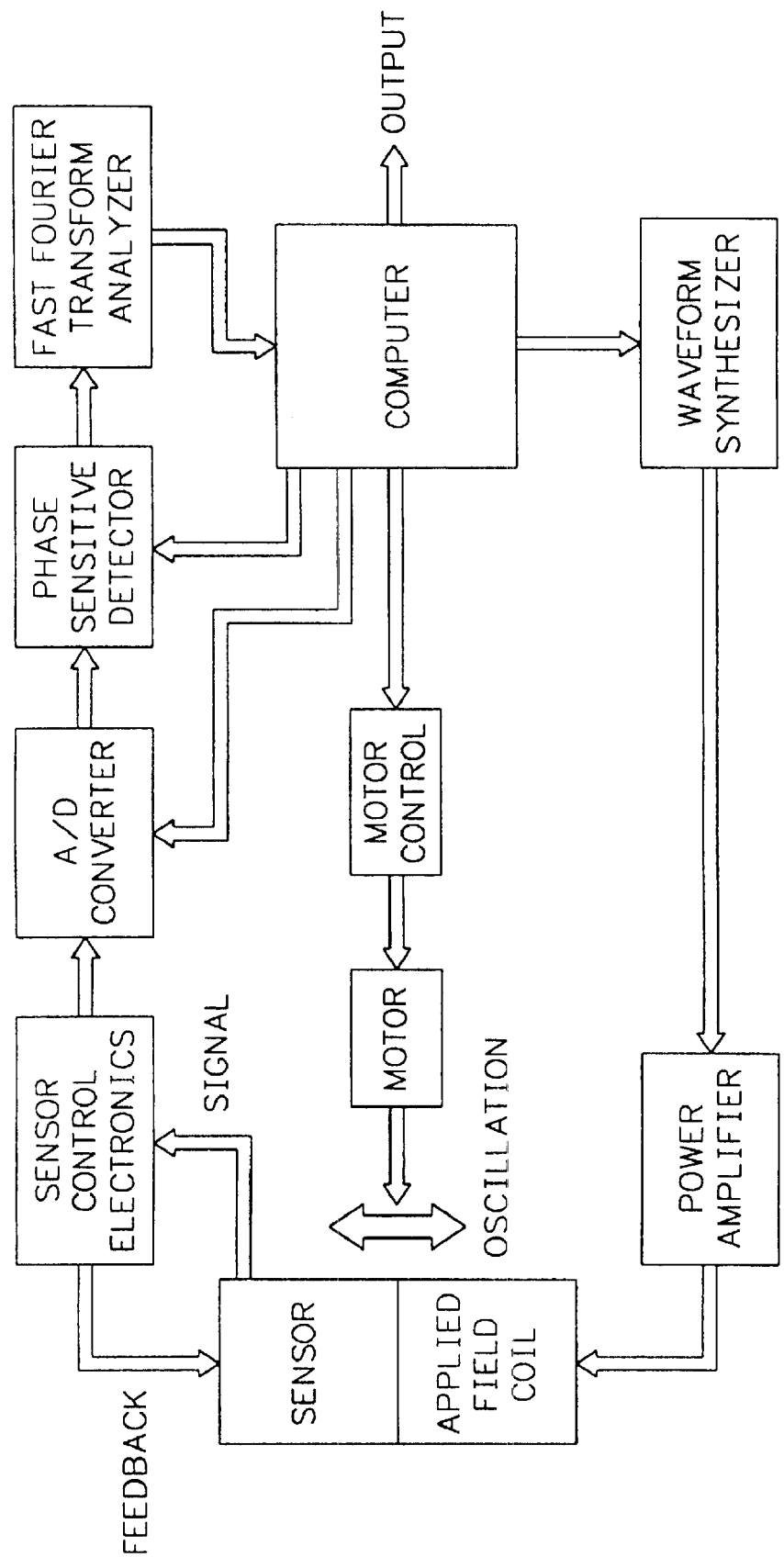
FIG. 6 shows a block diagram with the applied field current source and analyzing components used in the probing instrument.

FIG. 6 shows the computer analyzer, electronics, and control functions which process response signals from the sensor 24, and output information regarding the magnetic susceptibility of materials in the patient's body. A signal source is used to generate an AC signal between 25 Hz and 2 kHz. This signal, amplified by an audio frequency amplifier, provides a constant amplitude oscillating current through the applied field coils on the detection head assembly. A phase sensitive detector measures the component of the output of the magnetic sensor that oscillates in phase with an AC applied field. A Fourier transform analyzer calculates the component of the output of the phase-sensitive detector that oscillates in phase with the modulation of the sample-sensor distance. This provides a way to distinguish the signal of interest from the low-frequency noise caused by thermal drifts. The function of the phase sensitive detector can be performed by a lock-in amplifier, and the function of the Fourier transform analyzer can be performed by a spectrum analyzer. Preferably, either or both functions can be performed on a computer. The computer integrates and controls all instrument functions, including the modulation of the sensor-sample distance, the generation of the AC field coil current, and the processing of the magnetic sensor outputs to determine the magnetic susceptibility of the sample. The computer can be a personal computer with the required functioning signal cards and processors included. The motor indicated in FIG. 6 is preferably used to move the detector assembly toward and away from a patient's area of interest. The fast Fourier transformer is used to resolve the variation of the received signal in synchrony with this motion. The waveform synthesizer is used to generate an AC signal, which is then amplified by the power amplifier to generate an AC current for the applied field coil. The waveform synthesizer function can be incorporated by the computer. The AC signal can have frequencies up to around 2,000 hertz, preferably avoiding harmonics of the power line frequency. The AC signal can be synchronized with the power lines, at a frequency commensurate with the power line frequency, in order to minimize noise due to the power lines.

Actual output from the computer can be a data storage device, a video display of useful medical information, or a connection to a computer system network.

Figure 7:
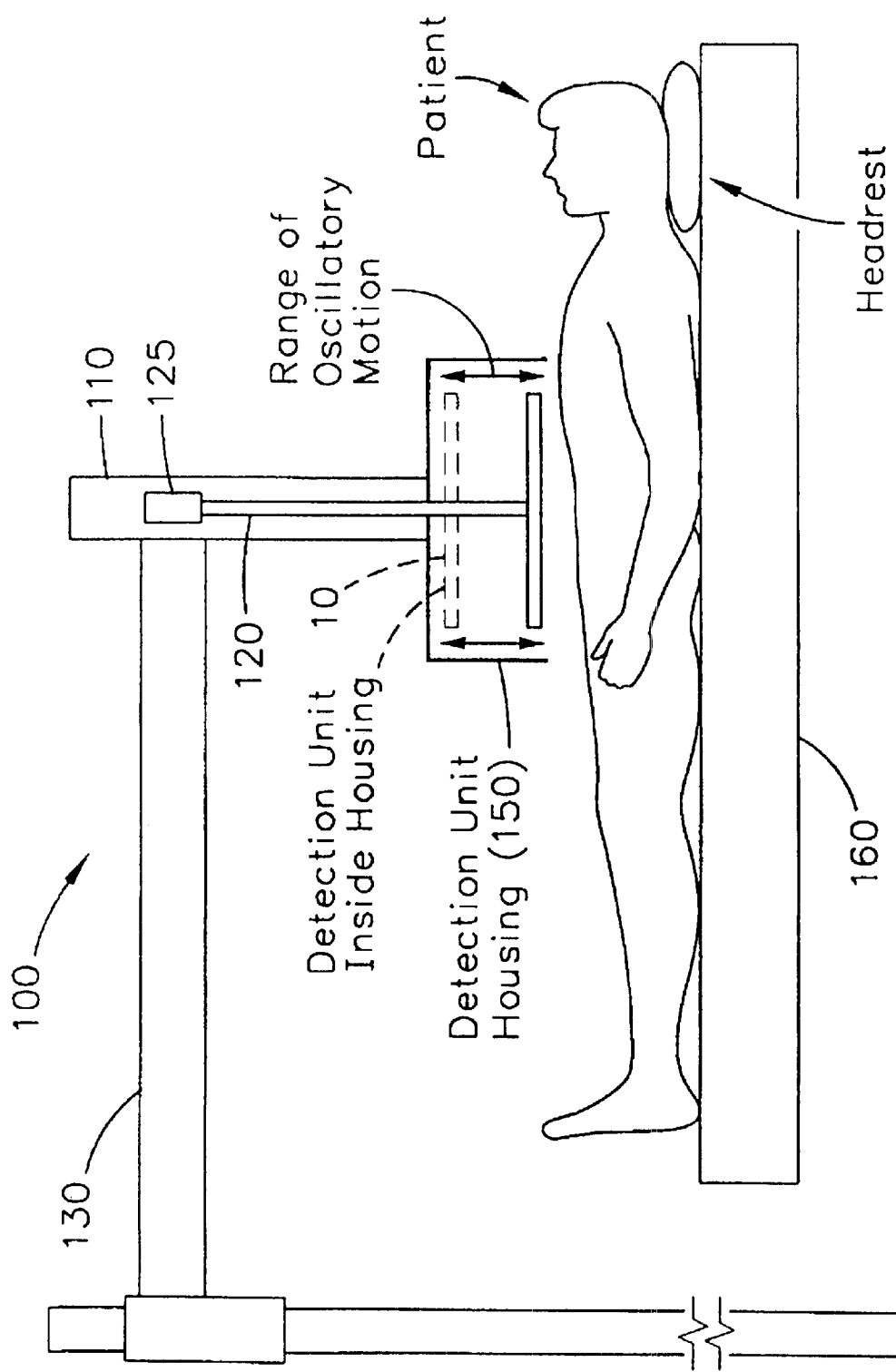
FIG. 7 shows an exemplary perspective view of the probing instrument.

The magnetic sensor control electronics, a motor/crank rod arrangement for oscillatory movement of the instrument's distal end detector assembly, a waveform synthesizer and power amplifier, a lock-in amplifier, and a spectrum analyzer or equivalent computer device for signal analysis can be incorporated in a single medical instrument unit as shown in exemplary form in FIG. 7 as unit 100. FIG. 7 shows the probe instrument 100 with an elongated positioning arm 130 wherein the detector assembly 10 is mounted at the distal end of the arm 110 which has a motor 125 within, with the required oscillatory drive members 120 that move the detector assembly 10 toward and away from a patient.

FIG. 7 shows the patient on a non-metallic table. The detector assembly 10 is positioned over a tissue area of interest. The detector assembly 10 has the sensor mounted to a reciprocating member 120 located within the arm 110 that can move the detector assembly 10 translationally toward and away from the distal end of the head member, preferably between one and six inches. The reciprocating action typically is in a range between around 0.5 and 10 hertz such that modulation of the detector assembly 10 filters out signal noise caused by temperature drifts in the applied field coils. When the temperature drifts are sufficiently low, modulation frequencies in the lower end of this range are desirable to reduce mechanical stresses on the detector assembly.

The reciprocating member 120 within the arm of the probe instrument 100 allows modulation of the distance between the examined tissue and the detector assembly 10, as explained above. Those portions of the reciprocating-motion mechanism in proximity to the detector assembly are made of nonmagnetic materials. In use, a water bag (not shown) may be placed between the detector assembly 10 and the patient.

Analysis is performed on the signal detected by the sensor to provide output information corresponding to the magnetic susceptibility of items detected in the area of interest.

Variations to the invention include the following:
a) Modulation of the distance between the sample and the detector assembly can improve the signal-to-noise ratio of magnetic susceptibility measurements on any type of sample (i.e., including samples other than the human body).
b) The methods and apparatus described in the parent U.S. patent application Ser. No. 08/670,393, now U.S. Pat. No. 5,842,986, can be modified by the modulation of the sample-sensor distance to improve the signal-to-noise ratio of magnetic susceptibility measurements for the detection of ferromagnetic foreign bodies (FFBs) within the eye, brain, or body of a patient.

The concentric-loop coil design (FIG. 5) may be used with the apparatus and methods described in the parent U.S. patent application Ser. No. 09/135,890, now U.S. Pat. No. 6,208,884, for the detection of ferromagnetic foreign bodies (FFBs) within the eye, brain, or body of a patient. The use of the concentric-loop coil can potentially improve the detection of FFBs located deep below the surface of the patient's face, head, or body.

Figure 8:
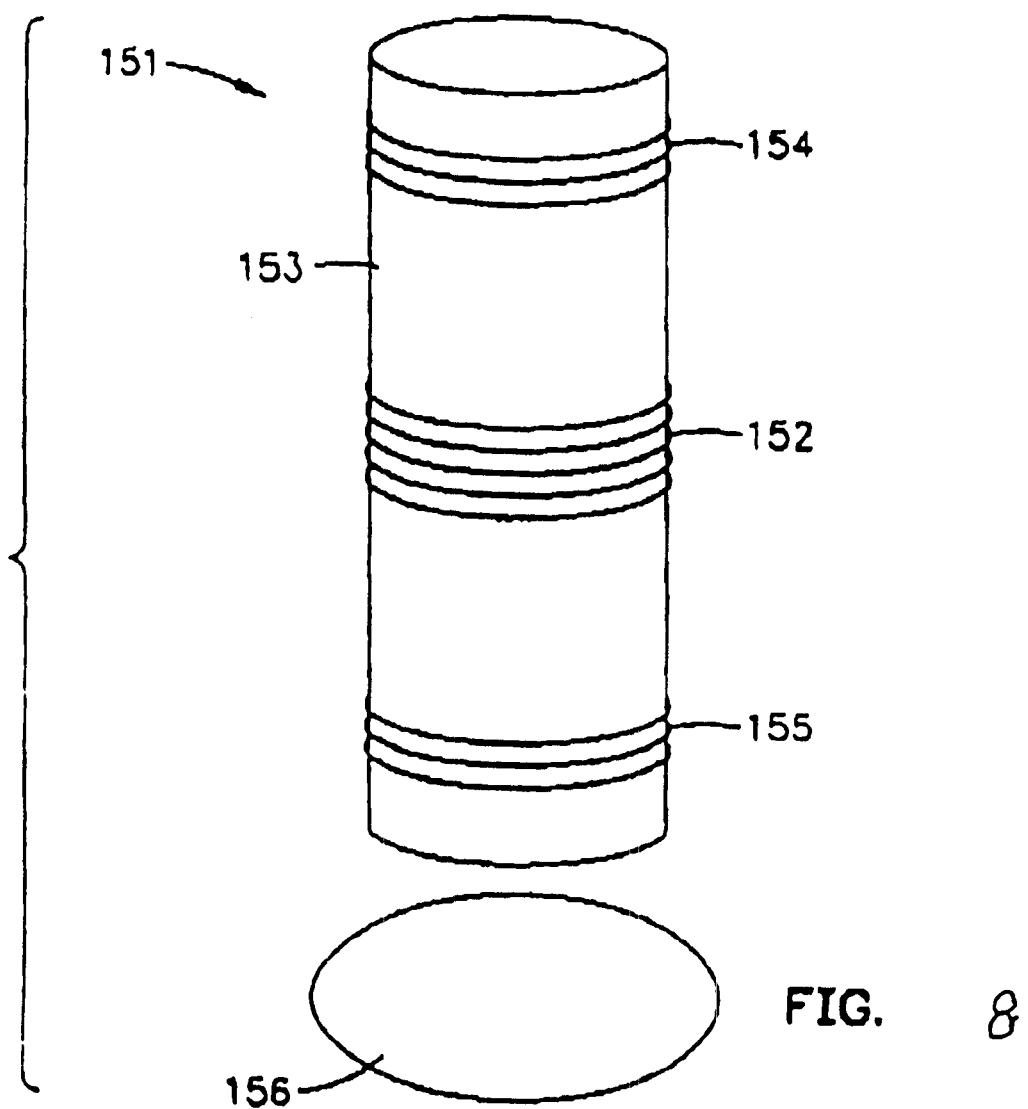
FIG. 8 shows an alternate embodiment which uses a gradiometer technique to cancel the signal due to the applied magnetic field, as disclosed in U.S. patent application Ser. No. 09/818,700.

FIG. 8, as disclosed in U.S. patent application Ser. No. 09/818,700, shows an alternative embodiment applicable for FFB detection, which uses a different technique to cancel the signal due to the applied magnetic field. As shown in FIG. 8, sensor unit 151 includes applied field coil 152 consisting of a coil wound on a coilform 153 made of a non-magnetic and non-metallic material, such as fiberglass. The sensor comprises two equal and oppositely wound coils 154 and 155 which are configured symmetrically about applied field coil 152, both physically and electrically. This arrangement of the sensor coils constitutes a first-order gradiometer. Because of the symmetry of the sensor coils about applied field coil 152, they sense approximately the same amount of magnetic field. Moreover, because the two sensor coils are equally and oppositely wound, the induced voltage in each of them due to an AC magnetic field from the applied field coil is equal but opposite in sign. Hence, the net voltage across both the sensor coils is substantially zero or close to zero, and the sensor coils are insensitive to the field applied by the applied field coil.

In order to measure the magnetic response from a sample, the sensor unit 151 can be positioned with respect to sample 156 as shown in FIG. 8. This results in sensor coil 155 being closer to the sample compared to sensor coil 154. Hence, the magnetic response of the sample is sensed at sensor coil 155 more strongly than that at coil 154. Correspondingly, the voltage induced at coil 155 is larger than that induced at coil 154. This results in a net voltage induced across the sensor coils. Therefore the gradiometer arrangement of the sensor coils allows for rejection of the response due to the applied field coil while at the same time being sensitive to the magnetic response from the sample. A similar result will be obtained by placing the sample close to coil 154 instead of coil 155.

Those skilled in this art will realize that there are other gradiometer configurations with more than two sensor coils which also provide for the rejection of the applied field while at the same time being sensitive to the signal from the sample. An example of such alternative configurations would use an applied-field coil wound as a first-order gradiometer, and a detection coil wound as a second-order gradiometer. In such a design, the detection coil would comprise two coils with equal areas and numbers of turns, wound in the same direction and placed at each end of the coil form, in series with a second coil, midway between the first two, which is wound in the opposite direction and has twice the number of turns as the first two coils. The applied-field coil would comprise two oppositely wound loops of equal area and having equal numbers of turns, placed at equal distances from the center coil of the second-order gradiometer.

In order to improve the sensitivity of the magnetic susceptibility measurements, sensor unit 151 can be reciprocated with respect to the sample. This reciprocating action allows for the mitigation or elimination of noise due to thermal effects.

In both the gradiometer design and in the applied-field coil designs described above, the signal due to the applied field is mostly cancelled due to the geometry of the applied-field coils and magnetic sensors. However, this cancellation is not usually complete, since it is not possible to achieve perfect symmetry in the construction of the sensors and applied-field coils. A variety of balancing techniques can be used to improve the cancellation of the applied-field signal. In order to minimize noise in the magnetic-field measurements, it is desirable to cancel both the in-phase and the out-of-phase components of the applied-field signal, with respect to the current in the applied-field coils. Methods to cancel the in-phase component include (1) connecting a small auxiliary coil in series with the applied-field coil, and adjusting its position with respect to the sensor or sensors, (2) using small, movable pieces of ferromagnetic material to adjust the magnetic field at the sensor(s) and (3) using a resistor network to sense the current in the applied-field coils and generate a compensating current in an auxiliary coil that couples to the sensor(s). Methods to cancel the out-of-phase component include (1) adjusting the position of loops or thin tabs of electrically conductive, non-ferromagnetic material, in such a way that currents in the loop or tab, induced by the applied ac field, produce an appropriate out-of-phase ac field at the sensor(s), and (2) placing an auxiliary coil in proximity to the sensor(s), connecting the auxiliary coil in series with a variable resistor, and adjusting the resistor so that currents induced in the auxiliary coil by the applied field produce an out-of-phase field of appropriate amplitude at the sensor(s). The in-phase and out-of-phase components of the field can also be cancelled by monitoring the current in the applied-field coil and using an analog circuit, digital processor or computer processing system to generate a current of appropriate phase and amplitude in an auxiliary coil that couples to the sensor(s). This electronic compensation can be operated as a feedback circuit to null out the response of the sensor(s). In order not to cancel out the response of the patient, this feedback circuit can operate with a time constant long compared with the reciprocating motion of the sensor unit. These residual field cancellation methods can be used with any of the embodiments of the sensor unit described herein.

For the detection of FFBs in the eye, brain, or body, the parent U.S. patent application Ser. No. 08/670,393 teaches the measurement of appropriate magnetic-field gradients, or alternatively, the mapping of the magnetic-susceptibility response as a function of position, in order to compute the location of the FFB within the host. This spatial mapping may be achieved either by using an array of more than one magnetic sensor, or by using a single magnetic sensor and moving the detection unit (applied field coils and magnetic sensor). Either approach may be used in conjunction with any of the applied-field coil designs described above.

The applied-field coil design of FIG. 5 may be modified to accommodate an array of more than one magnetic sensor. The parent U.S. patent application Ser. No. 08/670,393 discloses that to reduce the noise produced by variations in the applied magnetic field, it is desirable to ensure that the applied magnetic field is as small as possible at the location of each magnetic sensor. The concentric-loop coil described above cancels the magnetic field at a single point, the common center of the at least two concentric loops. If the radius of the inner coil is decreased slightly in relation to that of the outer coil, or if the current in the inner coil is increased slightly in relation to that of the outer coil, the magnetic field will be canceled not at a single point, but along a circle concentric with the two loops. Multiple sensors may then be placed at different locations on this circle, and the applied magnetic field will be canceled out at the location of each sensor. This arrangement makes possible the simultaneous measurement of the magnetic field response at multiple points in space.

As an alternative, the noise produced by applied-field variations may be minimized by measuring differences in magnetic field between two or more magnetic sensors, as long as the magnetic sensors are positioned within the applied-field coils in such a way that the applied magnetic field is the same for each of the sensors. Such a result may be achieved with an applied field coil consisting of a circular loop, or multiple concentric loops, by placing each of the magnetic sensors at the same distance from the center of the loop(s).

Moreover, the applied field coils of the concentric coil design shown in FIGS. 4 and 5 can have differing dimensions and configurations to measure at other tissue regions in the body. Also, switchable configurations of the applied field coil connections can be controlled by the instrument's computer allowing for adaptive control of the instrument for multiple examining capabilities.

Novel Water-Bag Method

One problem in sensitive magnetic susceptibility measurements on the human body is the very large response due to the magnetic susceptibility contrast between the body tissues and the surrounding air. This signal varies according to the shape of the body, and this variation can mask subtle changes in the magnetic susceptibility response due to variations in the magnetic susceptibility of the tissues, or, if applicable, the presence of small ferromagnetic foreign bodies. One method to reduce the magnetic susceptibility contrast problem is to insert a deformable water bag between the patient and the sensing apparatus.

In the traditional water-bag method, as commonly employed with SQUID sensor apparati, the sensing instrument is initially pressed against the patient's body. The patient is then moved away from the sensing apparatus, and the water bag is continuously supplied with water, such that the space between the sensing apparatus and the patient is filled with water at all times. With this method, the patient's body is, in effect, replaced by water throughout the field of view of the instrument, and the resulting change in magnetic susceptibility signal is due only to the difference in magnetic susceptibility between the body and water.

In the present method, as described in U.S. patent application Ser. No. 09/818,700, the water bag fills the space between the patient and a fixed, rigid barrier. Behind the barrier, the sensor unit is moved toward and away from the patient. The resulting change in the magnetic susceptibility signal contains a contribution due to the difference in magnetic susceptibility between water and the surrounding air. However, this contribution, which is defined by the shape of the fixed, rigid barrier, is the same for all patients. There is also a contribution due to the difference in magnetic susceptibility between the patient's body and water. This contribution may vary from patient to patient, and this variation contains information about the magnetic susceptibility of the sensed region of the body.

In essence, the traditional water-bag method eliminates the magnetic susceptibility signal due to the large susceptibility contrast between the water-like tissues of the body and the surrounding air. The present method does not eliminate this air-water magnetic susceptibility contrast, but rather replaces the varying shapes of the body surface with an air-water interface of constant shape defined by the rigid, fixed barrier.

Figure 9:
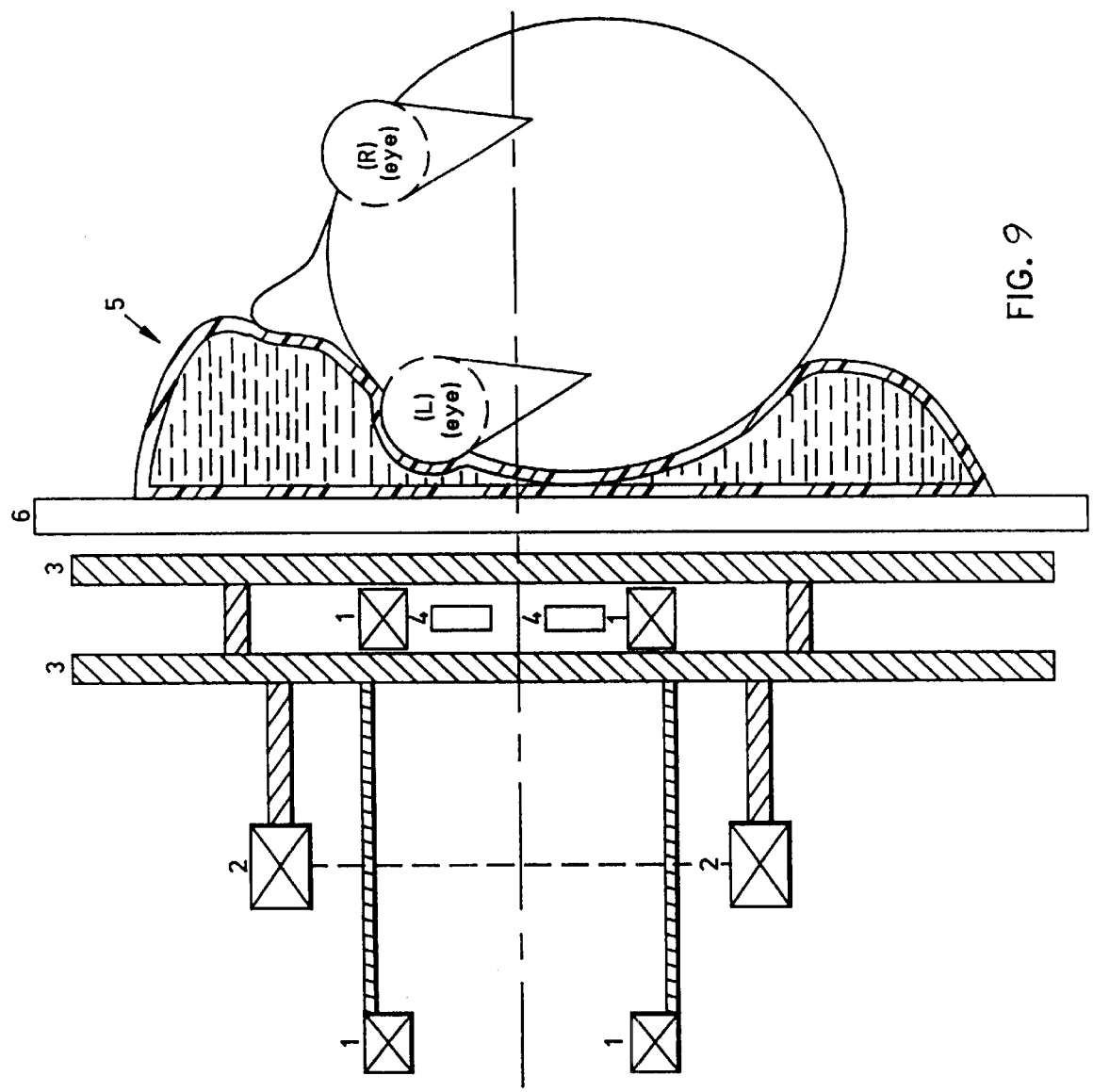
FIG. 9 shows features of the preferred magnetic susceptibility detector.

As shown in FIG. 9, in the apparatus of the present invention, gradiometer coils 1 sense magnetic field perpendicular to the sensed area of the body. The applied field coils 3, in a configuration similar to that illustrated in FIGS. 1 through 3, produce magnetic fields parallel to the sensed area of the body along two orthogonal axes, with a region of nearly zero magnetic field between the two applied field coils 3. Another applied-field coil 2 produces a magnetic field perpendicular to the sensed area of the body. Magnetic sensors 4 sense fields parallel to the sensed area of the body along two orthogonal axes. The sensed area of the patient's body is placed against a water or gel bag 5. A rigid barrier 6 separates the patient and the water bag from the detection apparatus.

The problem of discriminating between the magnetic susceptibility response of a ferromagnetic body and the background response due to surrounding material will now be discussed. Two types of discrimination techniques will be discussed. The first approach is based on statistical regularities in the response of the patient's body. The second approach uses a special combination of measurements to cancel out the response of weakly magnetic materials in the host, leaving only a signal due to the response of the FFB itself.

Discrimination Techniques Based on the Statistics of the Head Response

The simplest possible way to detect FFBs in the head is to measure the magnetic susceptibility response of the head, in a large number of people known not to have ferromagnetic foreign bodies. From these data, one skilled in the art can characterize the statistical variability of the response of the head itself. The simplest way to characterize that variability is simply to compute the mean and standard deviation of the head response for a sufficiently large, sufficiently representative population of normal subjects. Armed with this information, one can then detect patients with FFBs by looking for a magnetic susceptibility response that falls outside the normal range of variability. One might, for example, look for a magnetic susceptibility response that differs from the mean by more than a certain multiple of the standard deviation. That multiple of the standard deviation would be chosen to achieve a desired probability of detection without incurring excessive false alarm rates.

One can detect smaller FFBs by taking advantage of other statistical regularities in the response of the body. For example, in order to detect FFBs in the eye or orbit, one can take advantage of the symmetry between the right and left sides of the head. The magnetic susceptibility response of the head may vary considerably, according to size, shape and internal structure of the head. However, if one measures the magnetic susceptibility response at corresponding positions on the left and right sides of the head, the two measurements will be approximately the same for most people. More importantly, over a population of subjects, the standard deviation of the difference between right and left will generally be much smaller than the standard deviation of the head response itself. One can then detect an FFB in one eye, or on one side of the brain, by measuring the susceptibility response on both sides of the head, and seeing whether the right-left difference falls outside the normal range of variation.

One can exploit other statistical regularities in the head response as well. For example, the magnitude of the head response may be statistically correlated with the size of the head. Then, by measuring the circumference or other dimensions of the head, one can obtain additional information that one can use, in effect, to correct for a portion of the variability of the head response. This statistical information can be exploited using a variety of methods, including artificial intelligence, neural network and Bayesian techniques. Another approach is to develop a parameterized model which expresses the mean head response as a function of the dimensions of the head, and then subtracts out this mean response from the measured data.

Special Discrimination Technique for Elongated or Irregularly Shaped FFBs

With the methods described above, the smallest detectable FFB is limited by the statistical variability of the head response from person to person. The following paragraphs describe a different approach, in which one can cancel out the response of the head, without canceling the signal from the FFB itself. One can achieve this background cancellation by exploiting a characteristic difference between the magnetization response of the FFB and that of the tissues of the head.

In the following discussion, it is important to understand the distinction between the magnetization response and the magnetic field response. The term "magnetization response" means the magnetic moment per unit volume that is induced by the applied magnetic field, in any material present in the sensed region. This material may include either body tissues, or any foreign bodies that may be present. The terms "magnetic response" and "magnetic field response" mean the magnetic field detected by the magnetic sensor(s), which results from the magnetization response of materials present in the sensed region. What we measure is the magnetic field response, that is, the magnetic field produced by the magnetization response of all materials present in the sensed region. We reject that magnetic field response if, upon examining the data, we find certain mathematical regularities that arise when the underlying magnetization has two properties characteristic of biological tissues. Those two properties are (1) that the magnetization is in the direction of the applied field and (2) that the magnitude of the magnetization is independent of the direction of the applied field.

Body tissues, being diamagnetic, respond isotropically to an applied magnetic field. That is, the magnetization in the body tissues is always in the direction of the applied magnetic field, and the magnitude of the magnetization is independent of the direction of the applied field. In contrast, a ferromagnetic body can respond anisotropically to the magnetic field; its magnetic moment need not be aligned with the applied magnetic field, and its magnetic moment may vary in magnitude according to the orientation of the applied field. This anisotropic magnetic response depends on the shape of the FFB. A highly symmetrical ferromagnetic body, such as a sphere or cube, will respond isotropically, just as body tissues do. However, a very long, very thin ferromagnetic body responds in a very anisotropic way; its magnetic moment lies along its own long axis, not the direction of the applied field, and the magnetization varies in magnitude according to the component of the applied magnetic field along the long axis. In general, an FFB of arbitrary shape will have a magnetic moment that does not always lie parallel to the applied magnetic field, and whose magnitude varies to some degree with the direction of the applied magnetic field.

This direction-dependent magnetization response is what causes the FFB to rotate in order to align itself with the applied magnetic field. Consequently, when a patient is placed inside an MRI magnet, the FFBs most likely to cause tissue damage are the ones that respond in an anisotropic way to an applied magnetic field. By making use of this characteristic anisotropic response to distinguish the FFB from the background response of body tissues, one can enhance the detection of the FFBs that represent the greatest hazard to the MRI patient. The following paragraphs describe a special combination of measurements that cancels the isotropic response of body tissues, without canceling the anisotropic response of an FFB.

To show how this background cancellation can be accomplished, we first show that the response of the weakly magnetic host material has certain special symmetries, as a function of the directions of the applied and detected magnetic fields. We then show that these special symmetries are not true for a ferromagnetic body.

First consider the magnetization response of a weakly magnetic material, such as the tissues in the patient's head. If one applies a magnetic field to the head, the magnetization of the tissues at any point r is given by $$M(r)=\chi(r)H(r) \quad (1)$$

where $\chi(r)$ is the magnetic susceptibility of the tissues and $H(r)$ is the total magnetic field at each point in the head. In general, $H(r)$ is the sum of the applied field $H_0$, plus the field $H_{mag}(r)$ due to the magnetization of the tissues:

$$H(r)=H_0+H_{mag}(r) \quad (2)$$

However, the tissues of the body have a very weak magnetization response, characterized by $\chi$ much smaller than one. In this case, $H_{mag}$ is much smaller than $H_0$ (by several orders of magnitude, in the case of body tissues). Consequently, to a very good approximation, $$M(r) \cong \chi(r)H_0(r) \quad (3)$$

That is, because the magnetization of the body tissues is so weak, the magnetization is simply proportional to the applied magnetic field. Because the magnetic properties of the tissues are isotropic, the proportionality constant $\chi(r)$, is simply a scalar quantity, independent of direction. Consequently, the magnetization is always aligned with the applied field and has a magnitude independent of the direction of the applied field.

In the magnetic susceptibility measurement, a magnetic sensor is used to detect the magnetic field produced by the magnetization of the head. This field is given by $$B=(\mu_0/4\pi)\int dr[3(M\cdot r)r/r^5-M/r^3]=(\mu_0/4\pi)\int dr\chi(r)[3(H_0\cdot r)r/r^5 - H_0/r^3], \quad (4)$$

where r is the magnitude of the position vector r. In this expression, the integration is over the entire volume of the head, and it is assumed that the magnetic sensor is at a point r=0, which lies outside the head. In this measurement, one can apply the magnetic field in each of the three orthogonal directions, and measure the magnetic field in each of the three orthogonal directions. Let $B_{ij}$ be the magnetic field measured in the i direction, as a result of applying the magnetic field in the j direction. Then, $$B_{ij}=(\mu_0/4\pi)H_0\int dr\chi(r)(1/r^3)[3r_ir_j/r^2-\delta_{ij}]. \quad (5)$$

From this expression, it follows that the matrix $B_{ij}$ has the following symmetries:

$$B_{ij}=B_{ji},$$

and $$Tr(B_{ij})=B_{xx}+B_{yy}+B_{zz}=0. \quad (6)$$

That is, if one considers only the magnetic response of the body tissues themselves, the matrix $B_{ij}$ is symmetric and traceless.

This basic result applies not only to body tissues, but to any material in which the magnetic susceptibility $\chi$ is much less than one, and independent of the direction of the magnetic field. These properties are characteristic of all diamagnetic materials, including essentially all body tissues, as well as most paramagnetic and superparamagnetic materials.

The special symmetries expressed in Eq. (6) are not, in general, true for a ferromagnetic material. In this case, $\chi$ is much larger than one, and the approximation made in Eq. (3) is no longer valid. As a result, the magnetization of a ferromagnetic body often depends strongly on the shape of the body. For example, if the FFB is a very long, very narrow body oriented in the z direction, the matrix $B_{ij}$ takes the form $$\begin{bmatrix} B_{xx} & B_{xy} & B_{xz} \\ B_{yx} & B_{yy} & B_{yz} \\ B_{zx} & B_{zy} & B_{zz} \end{bmatrix} = CH_0 \begin{bmatrix} 0 & 0 & 0 \\ 0 & 0 & 0 \\ 3xz/r^2 & 3yz/r^2 & 3z^2/r^2-1 \end{bmatrix}, \quad (7)$$

where x, y and z are the coordinates describing the location of the FFB, $r=(x^2+y^2+z^2)^{1/2}$, and C is a constant determined by the size and magnetic susceptibility of the FFB. This matrix is neither symmetric nor traceless, that is, $B_{ij}$ is not equal to $B_{ji}$, and the sum of the matrix elements along the diagonal is not equal to zero.

In general, for an FFB of arbitrary shape, the magnetic moment of the FFB, $m_i$, will be related to the applied field by a matrix $C_{ij}$. That is, $$m_i = \sum_{j=1}^{3} C_{ij} H_j, \qquad (8)$$

where $H_j$ is the applied magnetic field in the j direction. Here, as in the discussion above, the indices i and j indicate the direction (x, y, or z) of the applied or detected magnetic field. By diagonalizing the matrix $C_{ij}$ one can define three principal axes for the FFB, corresponding to the three eigenvectors of the matrix $C_{ij}$. If one applies a magnetic field along any of these principal axes, the magnetic moment of the FFB will lie along the same axis, and its magnitude will be given by the corresponding eigenvalue of the matrix. For FFBs with very symmetrical shapes, all three eigenvalues will be the same, and the magnitude of the magnetic moment of the FFB will be independent of the direction of the applied field. In such cases, the magnetic response matrix $B_{ij}$ will be symmetric and traceless, as it is for the response of the body tissues alone. In general, however, the three eigenvalues will be different, and the matrix $B_{ij}$ will not be traceless or symmetric.

This analysis yields a method for canceling the response of body tissues and detecting the magnetic response of a ferromagnetic foreign body. A magnetic field is applied to the head, in each of the three mutually orthogonal directions. In each case, the magnetic field produced by the response of the head is measured in all three directions. One then tests whether the matrix $B_{ij}$ is symmetric and traceless. That is, one calculates the four quantities $B_{xy}-B_{yx}$, $B_{yz}-B_{zy}$, $B_{zx}-B_{xz}$, and $B_{xx}+B_{yy}+B_{zz}$. If any of these quantities is nonzero, it indicates the presence of a ferromagnetic foreign body whose magnetic moment varies according to the orientation of the applied magnetic field. This method detects any FFBs for which at least one of the eigenvalues of the magnetic response matrix $C_{ij}$ is sufficiently different from the other two.

The method described in the previous paragraph involves measuring the magnetic field response in all three directions for each of the three directions of the applied field. This approach maximizes the probability of detecting FFBs of all possible shapes, orientations, and locations. However, useful information can be derived by measuring only the field response in the direction of the applied field, so as to derive sufficient information in order to evalute the quantity $\text{Tr}(B_{ij})$. Similarly, useful information can be derived by measuring magnetic field components perpendicular to the applied field in order to evaluate one or more of the quantitites $B_{ij}-B_{ji}$, where i is not equal to j.

For FFBs of particular shape, orientation, and location, it is possible for one or more of the quantities $\text{Tr}(B_{ij})$, and $B_{ij}-B_{ji}$, to be zero, even though the FFB has an anisotropic response. The probability of detecting an FFB is increased when we measure all three components of the magnetic field response for each of the directions of the applied magnetic field, so as to determine all the quantities $\text{Tr}(B_{ij})$, and $B_{ij}-B_{ji}$. For certain very specific combinations of shapes, orientations, and locations, it is possible for all of these quantities to be zero, so that the FFB is not detected by this discrimination technique. However, this situation can be avoided by varying the location of the magnetic sensors in relation to the location of the FFB, either by moving the magnetic sensors relative to the position of the sensed body tissue, or moving the sensed body tissue, such as the eye, relative to the position of the magnetic sensors. In the detection of FFBs in the globe of the eye, for instance, the probability of detecting an FFB can be enhanced by having the patient move the eye in all directions.

The previous section describes a method for canceling the magnetic susceptibility response of the patient's head, in order to detect the response of an elongated or irregularly shaped FFB. The following paragraphs described preferred configurations for the coils that produce the applied fields, the magnetic sensors used to detect the response, and the sequence in which the fields are applied in each of the three orthogonal directions.

The discrimination technique described in the previous section requires that we apply magnetic fields in three orthogonal directions to the patient's head. In order to use the discrimination technique described above, it is important that the applied magnetic fields be as uniform as possible, and that each of the three applied fields be orthogonal to the other two. The following discussion indicates some of the factors to be considered in choosing the coil dimensions to achieve sufficient field uniformity.

As indicated by Eq. (5) above, the magnetic susceptibility response of the head includes contributions from every portion of the head. The response of the head, as described by the matrix $B_{ij}$ is symmetric and traceless only if the applied magnetic field is uniform throughout the head. However, the main contributions to the susceptibility response come from those portions of the head closest to the magnetic sensors. The contribution from a given small volume of the head falls off as $1/r^3$, where r is the distance from the sensors. With an applied field coil of finite size, the magnetic field is most nearly uniform within a certain central region, and deviates more and more from uniformity at increasing distances from that central region. In the preferred coil design, the magnetic sensors are placed in the region of maximum uniformity, and the overall dimensions of the coils are large enough so that the deviations from uniformity do not grow too rapidly with distance, in relation to the $1/r^3$ falloff of the sensitivity of the sensors. In practice, the uniformity of the applied fields can be evaluated by computing the quantities $B_{xy}-B_{yx}$, $B_{yz}-B_{zy}$, $B_{zx}-B_{xz}$, and $B_{xx}+B_{yy}+B_{zz}$ for a realistic representation of the head. The applied fields are sufficiently uniform if these quantities are small in comparison with the response of FFBs that the instrument is intended to detect.

In implementing the discrimination technique described above, it is preferable to measure the magnetic field response at the same location, for each of the three directions in which the field is measured. Magnetoresistive sensors are particularly advantageous for this purpose because their small size makes it possible to place them very close together. However, other types of sensors may be used, including fluxgate sensors, coils of wire, giant magnetoresistance sensors and spin-tunneling sensors.

The discrimination technique described in the previous section requires that we apply magnetic fields along each of the three orthogonal directions. The following paragraphs describe preferred sequences in which to apply the three magnetic fields.

In one preferred embodiment, the fields are applied sequentially in each of the three directions. This approach ensures that there is no difficulty in sorting out the responses produced by each of the three possible applied-field directions. A potential disadvantage of this method is that the symmetry and tracelessness of the matrix $B_{ij}$ may be compromised if the patient's head moves between measurements. This difficulty can be mitigated by applying the fields in short pulses, switching rapidly from one direction to the next, quickly enough so that the patient does not move very much between measurements. This sequence is then repeated continuously for as long as required for data averaging. For example, using 90-Hz AC fields, one might apply the fields in pulses 0.1 to 1 second long, so that the entire sequence of x, y and z directions is repeated every 0.3 to 3 seconds.

In a second preferred embodiment, AC fields are applied simultaneously in all three directions, using a different frequency for each field direction. In this scheme, the magnetic sensor outputs contain components at each of the frequencies, and the component at each frequency represents the magnetic susceptibility response generated by the applied field in the corresponding direction. This method allows measurement of all components of the response matrix $B_{ij}$ at the same time, eliminating errors due to motion of the subject's head. With this method, it may be useful to repeat the measurements three times, assigning each frequency to a different field direction each time, acquiring data at each frequency in each field direction, and thus eliminating any possible errors due to frequency-dependent effects.

In general, fields can be applied in the three directions using a wide variety of time dependencies, so long as the time dependencies for different axes are orthogonal as functions of time. That is, if $B_i(t)$ and $B_j(t)$ represent the time-dependent fields applied along two orthogonal directions, then $B_i(t)$ and $B_j(t)$ are orthogonal, if $$\int_{t}^{t+T} B_i(t) B_j(t) dt = 0, \quad (9)$$

where T is the length of time over which the measurements are taken. Each of the two preferred embodiments described above meets this orthogonality requirement.

Data Analysis Combining both Discrimination Techniques

All of the discrimination techniques described above can be combined within a single framework using standard methods of data analysis. For example, suppose we measure all nine components of the magnetic-field response $B_{ij}$ on both sides of the head, for a total of 18 measurements. Measuring these quantities on a population of subjects known not to have FFBs, we could calculate the covariance matrix of the 18 quantities over this population of normal subjects. Following the standard methods of multivariate statistics, we could find the eigenvectors and eigenvalues of the covariance matrix, thus defining an 18-dimensional probability distribution for all the measured quantities in the population of normal subjects. The surfaces of constant probability would be 18-dimensional ellipsoids, whose principal axes corresponded to the eigenvectors of the covariance matrix. This probability distribution would be especially narrow in certain directions within the 18-dimensional space, corresponding to special linear combinations of the 18 measured quantities. These special combinations of variables would include the differences in response between the right and left sides of the head, as well as the quantities $Tr(B_{ij})$ and $B_{ij} - B_{ji}$ defined above.

Based on this analysis, we would define a single quantity S, which described how far a given patient's measurements fell from the mean for the normal population:

$$S^2 = \sum_{n=1}^{18} (S_n - \bar{S}_n)^2 / 2\sigma_n^2,$$

where the $S_n$ represent the combinations of variables defined by the eigenvectors of the covariance matrix, $\bar{S}_n$ is the mean of $S_n$ and $\sigma_n^2$ is the variance of $S_n$ over the population of normal subjects. We would then define a threshold value of S, such that values below that threshold would be considered within the range of normal variation and values above that threshold would indicate the possible presence of an FFB. This analysis provides a single measure to determine whether a given patient falls outside the range of normal variation, taking into account the fact that certain combinations of measurements have relatively little variation within the population of normal subjects.

Other classification systems, such as neural network classification, linear regression, and statistical classifiers or discriminators, such as Bayesian classifiers, can also be useful in determining the presence or absence of an FFB. With each of these techniques, the probability of detection and the false-alarm rates may be improved by incorporating information that provides constraints upon, or characterizes the statistical distribution of, the response of the FFB itself.

The present invention can also be provided via a telemedicine and autointerpretation system which will help to reduce errors in diagnosis. This provides an integrated system for automated, computerized interpretation via a telemedicine vehicle, preferably, the Internet, of the test data obtained during the performance of the pre-MRI screening procedure. The data produced by the testing system are automatically reviewed and correlated with previously determined patterns recognized to be "normal", or "abnormal". Telemedicine is utilized to receive test data from the patient and to transmit the test interpretation, including the suspected presence of an FFB, and recommendations for any further clinical correlation required, or for further ancillary tests. This telemedicine system is "intelligent", in that ongoing data accumulation and analyses thereof improve the computational model and provide, over time, increasingly more accurate and sensitive ferromagnetic foreign-body detection. The interpretation system utilizes the results obtained from the pre-MRI screening test, which are converted into numerical representations for data processing. The central computer system is programmed to provide technically acceptable protocols for pre-MRI screening in order to obtain the highest quality test data, and, hence, the best possible autointerpretation test results.

While the particular invention as herein shown and disclosed in detail is fully capable of obtaining the objects and providing the advantages hereinbefore stated, it is to be understood that this disclosure is merely illustrative of the presently preferred embodiments of the invention and that no limitations are intended other than as described in the appended claims.

We claim:

1. A method for noninvasive screening of a human body for the presence of a ferromagnetic foreign body, said method comprising:

providing an instrument which includes at least one magnetic sensor, an applied field coil, and means for processing sensed signals from said at least one magnetic sensor;

positioning said instrument external to a patient in proximity to a region of interest;

supplying said applied field coil with current, thereby applying a magnetic field to said region of interest;

sensing a magnetic response from said region of interest with said magnetic sensor;

rejecting the magnetic response from biological tissues in said region of interest; and outputting data corresponding to the magnetic response of a ferromagnetic foreign body within said region of interest.

2. The method recited in claim 1, further comprising:

providing said applied field coil wound on a cylindrical coilform; and providing sensor coils axially spaced from said applied field coil on either side thereof;

wherein said sensor coils are oppositely wound in a gradiometer configuration.

3. The method recited in claim 2, further comprising positioning the instrument in proximity to the eye of the patient.

4. The method recited in claim 2, further comprising positioning the instrument in proximity to the brain of the patient.

5. The method recited in claim 1, further comprising positioning next to the patient a flexible bag substantially filled with deformable material having a magnetic susceptibility substantially similar to that of body tissue, said bag being attached to a substantially rigid barrier, said barrier being spaced from the patient by the flexible bag.

6. The method recited in claim 5, further comprising positioning the instrument in proximity to the eye of the patient.

7. The method recited in claim 5, further comprising positioning the instrument in proximity to the brain of the patient.

8. The method recited in claim 1, further comprising using a neural network for said rejecting of all magnetic responses from biological tissues in said region of interest.

9. The method recited in claim 1, further comprising using a Bayesian filter for said rejecting of all magnetic responses from biological tissues in said region of interest.

10. The method recited in claim 1, wherein:

said rejecting of said magnetic response from said biological tissues comprises rejecting, with said instrument, all magnetic responses within a statistically determined normal range of magnetic responses from said biological tissues in said region of interest; and said output data comprises indication of a magnetic response having a magnitude outside said normal range of magnetic responses from said biological tissues in said region of interest.

11. The method recited in claim 10, further comprising:

measuring magnetic responses of said region of interest in a statistically significant number of subjects to create a baseline of magnetic responses;

computing the mean and standard deviation of said baseline magnetic responses;

rejecting, with said instrument, all magnetic responses from said region of interest of the patient that fall within a selected number of standard deviations of said mean of said baseline magnetic responses; and indicating the presence of a ferromagnetic foreign body for any magnetic response that differs from said mean by said selected number of standard deviations.

12. The method recited in claim 11, wherein said selected number of standard deviations is empirically determined for each said region of interest.

13. The method recited in claim 12, wherein said selected number of standard deviations is between two and four.

14. The method recited in claim 10, further comprising:

measuring magnetic responses of two substantially symmetrical sides of said region of interest of the patient;

computing the difference between said magnetic responses of said two substantially symmetrical sides of said region of interest in the patient;

rejecting, with said instrument, all magnetic responses from said region of interest of the patient for which said difference between said magnetic responses of said two substantially symmetrical sides of said region of interest of the patient falls within a statistically determined normal range; and indicating the presence of a ferromagnetic foreign body for any magnetic response for which said difference between said magnetic responses of said two substantially symmetrical sides of said region of interest of the patient is outside said statistically determined normal range.

15. The method recited in claim 10, further comprising:

measuring magnetic responses of two substantially symmetrical sides of said region of interest in a statistically significant number of subjects;

computing the difference between said magnetic responses of said two substantially symmetrical sides of said region of interest in each said subject to create a baseline of magnetic response differences;

computing the mean and standard deviation of said baseline differences between said magnetic responses;

measuring magnetic responses of two substantially symmetrical sides of said region of interest of the patient;

computing the difference between said magnetic responses of said two substantially symmetrical sides of said region of interest in the patient;

rejecting, with said instrument, all magnetic responses from said region of interest of the patient for which said difference between said magnetic responses of said two substantially symmetrical sides of said region of interest of the patient falls within a selected number of standard deviations of said mean of said baseline differences; and indicating the presence of a ferromagnetic foreign body for any magnetic response for which said difference between said magnetic responses of said two substantially symmetrical sides of said region of interest of the patient differs from said mean of said baseline differences by said selected number of standard deviations.

16. The method recited in claim 15, wherein said selected number of standard deviations is empirically determined for each said region of interest.

17. The method recited in claim 16, wherein said selected number of standard deviations is between two and four.

18. The method recited in claim 10, further comprising:

measuring at least one dimension of said region of interest in a statistically significant number of subjects;

measuring the magnetic response of said region of interest in each of said subjects;

correlating each said magnetic response to each said at least one dimension of said region of interest;

measuring said at least one dimension of said region of interest of the patient;

measuring the magnetic response of said region of interest of the patient;

rejecting all magnetic responses from said region of interest of the patient which fall within a normal range of magnetic responses for said measured dimension of the patient; and indicating the presence of a ferromagnetic foreign body for any magnetic response having a magnitude above said normal range.

19. The method recited in claim 18, further comprising using a neural network for said correlating of each said magnetic response to each said at least one dimension of said region of interest, and for said rejecting of all magnetic responses from said region of interest of the patient which fall within a normal range.

20. The method recited in claim 18, further comprising using a Bayesian filter for said correlating of each said magnetic response to each said at least one dimension of said region of interest, and for said rejecting of all magnetic responses from said region of interest of the patient which fall within a normal range.

21. The method recited in claim 10, further comprising:

measuring all nine components of the magnetic-field response on both sides of said region of interest, for a total of 18 measurements, on each subject of a population of subjects known not to have FFBs;

calculating the covariance matrix of the 18 quantities over said population of normal subjects;

finding the eigenvectors and eigenvalues of said covariance matrix;

defining an 18-dimensional probability distribution for all the measured quantities in said population of normal subjects, wherein the surfaces of constant probability are ellipsoids, and where the principal axes of said ellipsoids correspond to the eigenvectors of said covariance matrix; and defining a threshold value of how far a given patient's measurements fall from the mean for the normal population, such that values below that threshold would be considered within the range of normal variation and values above that threshold would indicate the possible presence of an FFB.

22. The method recited in claim 1, wherein:

said rejecting of said magnetic response from said biological tissues comprises rejecting any magnetic response not indicating an item substantially subject to rotation by an applied magnetic field;

wherein said output data comprises indication of a magnetic response characteristic of a ferromagnetic foreign body subject to rotation by an applied magnetic field.

23. The method recited in claim 22, further comprising:

making said magnetic field substantially uniform and substantially unidirectional, in the region of interest;

applying said magnetic field to said region of interest in each of three mutually orthogonal directions;

sensing said magnetic response from said region of interest in the direction of said application of the applied magnetic field, for each said direction of application of said magnetic field; and rejecting any magnetic response of materials for which the magnitude of magnetization response does not substantially vary with the direction of said applied field.

24. The method recited in claim 22, further comprising:

making said magnetic field substantially uniform and substantially unidirectional, in the region of interest;

applying said magnetic field to said region of interest in each of three mutually orthogonal directions;

sensing said magnetic response from said region of interest in each of said three mutually orthogonal directions, for each said direction of application of said magnetic field; and rejecting any magnetic response of materials for which the magnitude of magnetization response does not substantially vary with the direction of said applied field.

25. The method recited in claim 24, wherein:

said rejecting of said magnetic responses comprises:

rejecting all magnetic responses in which the direction of said magnetization response is always in said direction of said applied field and in which the magnitude of said magnetic response is independent of said direction of said applied field; and said output data comprises:

indication of a magnetization response having a direction different from said direction of said applied field; and indication of a magnetization response having a magnitude substantially dependent upon said direction of said applied field.

26. The method recited in claim 24, wherein:

said three magnetic fields are applied simultaneously in said three mutually orthogonal directions;

each of said three magnetic fields is at a frequency different from the frequencies of the other two of said three magnetic fields;

said three magnetic responses in said three mutually orthogonal directions are sensed simultaneously, for each of said three magnetic fields; and said three magnetic responses resulting from each said applied field are sensed at the frequency of said applied field.

27. The method recited in claim 24, wherein:

said three magnetic fields are applied sequentially in said three mutually orthogonal directions; and said three magnetic responses in said three mutually orthogonal directions are sensed simultaneously, for each of said three magnetic fields.

28. The method recited in claim 1, further comprising outputting data corresponding to a magnetization response which is not parallel to said applied magnetic field.

29. The method recited in claim 1, further comprising outputting data corresponding to a magnetization response which has a magnitude that varies with the direction of said applied magnetic field.

30. A method for noninvasive screening of a human body for the presence of a ferromagnetic foreign body, said method comprising:

providing a test instrument at a remote location, including at least one magnetic sensor and an applied field coil;

providing a central computer system;

supplying said applied field coil with current, thereby applying a magnetic field to a region of interest of a patient;

sensing a magnetic response from said region of interest with said magnetic sensor;

transmitting said magnetic response to said central computer system;

rejecting said magnetic response from biological tissues, with said central computer system;

outputting data corresponding to the magnetic response of a ferromagnetic foreign body, with said central computer system; and transmitting said output data to said remote location.

31. The method recited in claim 30, wherein:

said rejecting of said magnetic response from said biological tissues comprises rejecting, with said central computer system, all magnetic responses within a statistically determined normal range of magnetic responses from said biological tissues in said region of interest; and said output data comprises indication of a magnetic response having a magnitude outside said normal range of magnetic responses from said biological tissues in said region of interest.

32. The method recited in claim 30, wherein:

said rejecting of said magnetic response from said biological tissues comprises rejecting, with said central computer system, any magnetic response not indicating an item substantially subject to rotation by an applied magnetic field;

said output data comprises indication of a magnetic response characteristic of a ferromagnetic foreign body subject to rotation by an applied magnetic field.

33. The method recited in claim 30, further comprising:

transmitting said magnetic response from said remote location to said central computer system via the Internet; and transmitting said output data from said central computer system to said remote location via the Internet.

34. A method for noninvasive screening of a human body for the presence of a ferromagnetic foreign body, said method comprising:

providing an instrument which includes at least one magnetic sensor, a permanent magnet, and means for processing sensed signals from said at least one magnetic sensor;

positioning said instrument external to a patient in proximity to a region of interest;

applying a magnetic field to said region of interest;

sensing a magnetic response from said region of interest with said magnetic sensor;

rejecting the magnetic response from biological tissues in said region of interest; and outputting data corresponding to the magnetic response of a ferromagnetic foreign body within said region of interest.

* * * * *